US011224628B2

(12) United States Patent
Garti et al.

(10) Patent No.: US 11,224,628 B2
(45) Date of Patent: *Jan. 18, 2022

(54) METHOD FOR EXTRACTION OF AN AGENT FROM A PLANT SOURCE

(71) Applicant: Yissum Research Development Company of the Hebrew University of Jerusalem Ltd., Jerusalem (IL)

(72) Inventors: Nissim Garti, Ramat HaSharon (IL); Sharon Garti Levi, Modi'in (IL); Rotem Edri, Eilat (IL)

(73) Assignee: YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 138 days.

This patent is subject to a terminal disclaimer.

(21) Appl. No.: 16/338,280

(22) PCT Filed: Sep. 28, 2017

(86) PCT No.: PCT/IL2017/051101
§ 371 (c)(1),
(2) Date: Mar. 29, 2019

(87) PCT Pub. No.: WO2018/061011
PCT Pub. Date: Apr. 5, 2018

(65) Prior Publication Data
US 2019/0314432 A1   Oct. 17, 2019

(51) Int. Cl.
*A23L 33/105*   (2016.01)
*A61K 36/05*   (2006.01)
*A61K 9/00*   (2006.01)
*A61K 31/122*   (2006.01)
*A61K 47/46*   (2006.01)

(52) U.S. Cl.
CPC ............ *A61K 36/05* (2013.01); *A23L 33/105* (2016.08); *A61K 9/0014* (2013.01); *A61K 9/0053* (2013.01); *A61K 31/122* (2013.01); *A61K 47/46* (2013.01); *A61K 2236/33* (2013.01); *A61K 2236/35* (2013.01)

(58) Field of Classification Search
None
See application file for complete search history.

(56) References Cited

U.S. PATENT DOCUMENTS

| | | | |
|---|---|---|---|
| 2006/0217445 A1* | 9/2006 | Chew | A61K 31/015 514/690 |
| 2007/0104741 A1 | 5/2007 | Murty et al. | |
| 2008/0279940 A1 | 11/2008 | Rigassi et al. | |
| 2008/0300386 A1* | 12/2008 | Lazarev | C07K 1/145 530/427 |
| 2012/0004319 A1* | 1/2012 | Shimizu | C12P 23/00 514/691 |
| 2013/0089600 A1 | 4/2013 | Winnicki | |
| 2016/0081927 A1 | 3/2016 | Bromley | |
| 2017/0042808 A1* | 2/2017 | Hirai | A61K 47/10 |
| 2017/0181940 A1* | 6/2017 | Richard | A61Q 19/00 |
| 2017/0232210 A1* | 8/2017 | Boeckl | A61P 1/04 128/203.15 |
| 2018/0042845 A1 | 2/2018 | Sinai et al. | |
| 2019/0231833 A1* | 8/2019 | Garti | A61K 9/7023 |

FOREIGN PATENT DOCUMENTS

| | | |
|---|---|---|
| CN | 1547479 A | 11/2004 |
| CN | 102145084 A | 8/2011 |
| CN | 103110582 A | 5/2013 |
| CN | 103690580 A | 4/2014 |
| CN | 104619318 A | 5/2015 |
| CN | 105535111 A | 5/2016 |
| CN | 105997985 A | 10/2016 |
| EP | 2 223 913 A1 | 9/2010 |
| IL | 165 528 A | 11/2010 |
| WO | 03/105607 A1 | 12/2003 |
| WO | 2006/094829 A1 | 9/2006 |
| WO | 2008/058366 A1 | 5/2008 |
| WO | 2013/044579 A1 | 4/2013 |
| WO | 2014/031504 A1 | 2/2014 |
| WO | 2015/011724 A2 | 1/2015 |

(Continued)

OTHER PUBLICATIONS

Patil P. et al. Phytosomes Increasing Bioavailability of Phytoconstituents. Int J of Universal Pharmacy and Bio Sciences 5(4)81-94, Jul. 2016. (Year: 2016).*

Amsalem et al., "Phospholipids-embedded fully dilutable liquid nanostructures. Part 2: The role of sodium diclofenac", Colloids and Surfaces B: Bioterfaces, (2010), vol. 81, No. 2, pp. 422-429.

Database Medline, Lu et al., Apr. 2009. "Study on extraction of quercetin in guava leaf by microemulsion" XP002776489.

Database Medline, Yue et al., May 2014. "Study on extracting and separating curcuminoids from Curcuma longa rhizome using ultrasound strengthen by microemulsion" XP002776488.

Deutch-Kolevzon et al., "Synergistic cosolubilization of omega-3 fatty acid esters and CoQ10 in dilutable microemulsions", Chemistry and Physics of Lipids, (2011), vol. 164, pp. 654-663.

(Continued)

*Primary Examiner* — Ralph J Gitomer
(74) *Attorney, Agent, or Firm* — Vorys, Sater, Seymour and Pease LLP; William L. Klima

(57) ABSTRACT

Provided is a process for extraction of a lipophilic agent from a plant source, the process including: mixing a first quantity of a plant source, the plant source being containing the lipophilic agent and a first quantity of an extraction medium to obtain a first mixture, the extraction medium being in the form of a microemulsion and comprising at least one oil, at least one hydrophilic surfactant, at least one co-surfactant and optionally at least one co-solvent; homogenizing the first mixture under conditions maintaining the microemulsion structure; and separating the homogenized mixture into a biomass slurry and an agent-loaded medium to obtain the agent-loaded medium in a microemulsion form.

14 Claims, 13 Drawing Sheets

(56) References Cited

FOREIGN PATENT DOCUMENTS

| WO | 2016/022936 A1 | 2/2016 |
| WO | 2018/061007 A1 | 4/2018 |
| WO | 2018/061009 A1 | 4/2018 |

OTHER PUBLICATIONS

Fisher et al., "Solubilization of simvastatin and phytosterols in a dilutable microemulsion system", Colloids and Sufaces B.: Biointerfaces, (2013), vol. 107, pp. 35-42.

Garti et al., "Nano-sized self assemblies of nonionic surfactants as solubilization reservoirs and microreactors for food systems", Soft Matter Journal, (2005), vol. 1, pp. 206-218.

Lee et al., "Comparison of the Antioxidant and Transmembrane Permeative Activities of the Different Polygonum cuspidatum Extracts in Phospholipid-Based Microemulsions", Journal of Agricultural and Food Chemistry, (2011), vol. 59, pp. 9135-9141.

Liu et al., "A new biocompatible microemulsion increases extraction yield and bioavailability of Andrographis paniculata", Chinese Journal of Natural Medicines, (2016), vol. 14, No. 9, pp. 683-691.

Spernath et al., "Microemulsions as carriers for drugs and nutraceuticals", Adv. in Colloid and Interface Science Journal, (2006), vol. 128, pp. 47-64.

Spernath et al., "Fully dilutable microemulsions embedded with phospholipids and stabilized by short-chain organic acids and polyols", Journal of Colloid and Interface Science, (2006), vol. 299, pp. 900-909.

Spernath et al., "Phase Transition Induced By Water Dilution In Phospholipid U-Tyoe Food-Grade Microemulsions Studied by DSC", Journal of Thermal Analysis and Calorimetry, (2006), vol. 83, Issue 2, pp. 297-308.

Spernath et al., "Phosphatidylcholine embedded microemulsions: Physical properties and improved Caco-2 cell permeability", Journal of Controlled Release, (2007), vol. 119, pp. 279-290.

Vandamme, "Microemulsions as ocular drug delivery systems: recent developments and future challenges", Progress in Retinal and Eye Research, (2002), vol. 21, No. 1, pp. 15-34.

Yang Hua et al., "Experiment of Extracting Salviae Miltiorrhizae on using O/W Microemulsion", China Journal of Chinese Materia Medica, vol. 33, Issue 22—English Abstract attached.

\* cited by examiner

METHOD FOR EXTRACTION OF AN AGENT FROM A PLANT SOURCE

TECHNOLOGICAL FIELD

The present disclosure provides methods for extraction of various agents, e.g. active agent, from a plant source, specifically with the use of extraction formulations which are based on micellar liquid systems.

BACKGROUND ART

References considered to be relevant as background to the presently disclosed subject matter are listed below:
[1] WO 2008/058366
[2] A. Spernath, A. Aserin, *Advances in Colloid and Interface Science* 2006, 128
[3] A. Spernath, A. Aserin, N. Garti, *Journal of Colloid and Interface Science* 2006, 299, 900-909
[4] A. Spernath, A. Aserin, N. Garti, *Journal of Thermal Analysis and calorimetry* 2006, 83
[5] N. Garti, A. Spernath, A. Aserin, R. Lutz, *Soft Matter* 2005, 1
[6] A. Spernath, A. Aserin, L. Ziserman, D. Danino, N. Garti, *Journal of Controlled Release* 2007, 119
[7] S. Fisher, E. J. Wachtel, A. Aserin, N. Garti, *Colloids and Surfaces B: Biointerfaces* 2013, 107, 35-42
[8] R. Deutch-Kolvzon, A. Aserin and N. Garti, *Chemistry and Physics of Lipids* 2011, 164(7), 654
[9] O. Amsalem, A. Aserin, N. Garti, Colloids and Surfaces, B: Biointerfaces 2010, 81(2), 422-429.

Acknowledgement of the above references herein is not to be inferred as meaning that these are in any way relevant to the patentability of the presently disclosed subject matter.

BACKGROUND

Extracts containing various agents from various plant sources have been used for many years in a plethora of applications, varying from cleaning and industrial applications to cosmetic and therapeutic uses.

One of the methods commonly used to extract lipophilic (or non-water soluble) active agents from plant sources is extraction by carrier oils, in which the carrier oil is used as a solvent for the extraction of the desired lipophilic species from the plant source.

Another method often used is extraction by organic solvents, which are selected amongst solvents capable of dissolving the desired lipophilic agent. Such extraction requires tailoring of the solvent for effective extraction of each lipophilic agent, and often result in low yields of extraction. Further, it is difficult to remove traces of the solvent from the end product, reducing the degree of purity and the safety of the resulting extract. Most of these extractions are found to be insufficient and often leave undesired traces of the solvent (especially when petroleum ethers are used). In most cases the extraction by conventional solvents is not selective, hence necessitating further processing to obtain the desired material. Further, in most cases the formulations show inconsistent or limited bioavailability.

A further method which is used for obtaining extraction of various compounds from various plant sources is supercritical $CO_2$ extraction. In the $CO_2$ extraction process, $CO_2$ at super-critical conditions (i.e. high temperature and pressure) is used as a solvent for the desired lipophilic species. Although very effective for extracting a variety of compounds from the plant source, this technique is often more complicated and very expensive compared to liquid extraction. In addition, this technique is far from being selective to specific lipophilic agents, and may concomitantly and indiscriminately extract other lipophilic products from the plant source.

Thus, there exists a need for a simple, highly-tailorable extraction process and extraction medium for extraction of desired agents from plant sources.

GENERAL DESCRIPTION

Efficient extraction of lipophilic (or water insoluble) agents from various natural sources is provided in the present disclosure by the use of a unique one-pot extraction process. As further detailed herein, the present disclosure also provides mediums enabling such extraction, as well as various pharmaceutical compositions and administration forms comprising it.

In one of its aspects, the present disclosure provides a lipophilic agent from a plant (i.e. natural) source, the process comprising:
(a) obtaining (for example, by mixing) a first mixture comprising a first quantity of a plant source containing the lipophilic agent and a first quantity of an extraction medium, the extraction medium comprising at least one oil, at least one hydrophilic surfactant and at least one co-surfactant, and optionally at least one co-solvent;
(b) homogenizing the first mixture; and
(c) separating the homogenized mixture into a biomass slurry and an agent-loaded medium.

In some embodiments, the lipophilic agent is not a cannabinoid.

The extraction media used in the processes of this disclosure show high extraction efficiency, high loading capacity, high selectivity, as well as being non-expensive and relatively easy to use.

The extraction media of this disclosure are substantially water-free micellar systems, which may be regarded as oil-in-oil microemulsions. Microemulsions (MEs) are well-known vehicles for delivery of drugs because of their spontaneous formation, high solubilization capacity, low viscosity, transparency and physical thermodynamic stability [1]. The extraction media of this disclosure are a specific, tailored type of microemulsion, which are an advanced category of delivery vehicles. These systems have been previously studied and their ability to solubilize non-soluble drugs and nutraceuticals has been demonstrated [2-7]. The extraction medium is a self-assembled microemulsion system of nanodroplets, comprising surfactants and oil. The extraction media of the present disclosure, as will be explained further herein, comprise at least one oil, at least one hydrophilic surfactant and at least one solvent, and may further comprise additional components such as co-surfactants, co-solvents and phospholipids. In the present disclosure, the term extraction medium will refer to such substantially water-free microemulsions, unless otherwise defined. The terms "microemulsion" and "extraction medium" will be used interchangeably.

The extraction medium may be in the form of water-free concentrates, that can be fully and progressively diluted with aqueous phase to form O/W microemulsions. The diluted medium (diluted microemulsion) are nano-sized uniform (mono-dispersed) structures, exhibiting zero interfacial tensions between the oil phase and the aqueous phase behaving like Newtonian fluids.

The extraction medium is self-assembled upon mixing the surfactants and the oil to form water-free reverse micelles.

Upon dilution with water or aqueous solutions, water-swollen micelles or water-in-oil nanodroplets are formed, being able to invert into bicontinuous mesophases in the presence of an aqueous phase, e.g. water. Upon further dilution, they undergo (umbrella type) inversion into oil-in-water droplets.

Without wishing to be bound by theory, the extraction media are constituted by oil-solvated clusters or short domains of surfactants, however differ from the classical reverse micelles. When mixed with small amounts of aqueous media, hydrated and solvated surfactants are formed, and upon further dilution with aqueous phase they are easily transform into oil-in-water (O/W) nanodroplets entrapping into their core the lipophilic agent molecules. The transformation to O/W microemulsions is spontaneous, i.e. without the need to employ shearing, mechanical forces or excessive heating conditions. The lipophilic agent is entrapped in the core of the reverse micelles and remains at the interface between the oil phase and the aqueous phase upon dilution during the bicontinuous region; thereafter lipophilic agent is located in the core of the droplets once the O/W microemulsion is formed (i.e. the diluted medium). The interactions (physical complexation) between the lipophilic agent and the surfactants (as well as the co-surfactants, when used) allow maintaining the lipophilic agent within the oil core throughout the structural transformations of the reverse micelles into a bicontinuous region and finally to the O/W microemulsion, thus stabilizing the formulation and preventing undesired release of the lipophilic agent from the oil core.

The extraction media may be designed to have chemical compatibility with the lipophilic agents to be extracted, thereby resulting in integration and interpenetration of the extracted lipophilic agent into the surfactant and co-surfactants that form the micelle. This helps to stabilize the loaded medium and supports high loading of the lipophilic agent within the oil droplets.

These media are thermodynamically stable, with nano-sized droplets, which may be safely stored for prolonged periods of time, without creaming, aggregation, coalescence or phase separation. The agent-loaded media prepared by the process of this disclosure are also characterized by a substantially uniform and stable droplets size, typically in the nanometric scale and having a narrow size distribution. The stability of the droplet size of the system is of importance, as changes in the droplet size may impair the release of the lipophilic agent entrapped (solubilized) within the droplets. Further, the lipophilic agent-loaded media, when not in diluted form, are substantially devoid of water, and as such do not support (or minimize) microbial growth. Further, due to their high stability and small droplet size, the systems may be sterilized without the risk of self-contamination in various ways, such as heat sterilization, filtration through a 0.22 μm filter, UV and other methods know to the art, without damaging the media's beneficial structure.

In the present disclosure, the extraction media are designed (i.e. by tailoring the composition of the surfactants, oil and co-surfactants) to extract various lipophilic agents from a variety of plant source, such that the loaded system (agent-loaded medium) is substantially water-free (at times devoid entirely of water or even anhydrous), which can be easily diluted or further formulated "on demand" and as per application or route of administration with any type of aqueous solution (buffer, water for injection, saline, isotonic mixtures and others).

The lipophilic agent generally refers herein to compounds which are water insoluble, and may dissolve in fats, oils, lipids, non-polar solvents and other specific solvents (such as acetone, DMF, DMSO, DMA). Such agents may include, for example, astaxanthin, lycopene, beta-carotene, lutein, eugenol, piperine, anthocyanins, betain, oleuropein, trimyristin, curcumin, capsaicin, gossipol, rosmanol, chlorogenig acid, cynamaldehyde, flavones, caffeine, isoflavone, tocopherol, omega fatty acids (including DHA and EPA), chlorogenic acid, caffeic acid, niacin, nicotinamide, falvanoids, cineole, borneol, thujone, carnosol, carnosic acid, fumaric acid, behenic acid and similar triglycerides and esters of long chain fatty acids or their corresponding triglyceride.

In the context of the present disclosure, the term is meant to encompass also isomers, derivatives, analogues or precursors of these agents.

When referring to the plant source, it is to be understood that the raw-material from which the lipophilic or water insoluble agent is extracted in a plant or a vegetative material. It is to be understood that the term also means to encompass extractable raw material being or derived from algae, microalgae, fungus, mold, yeast, etc. The plant source may be any naturally-occurring strain, any horticultural variant, cultivated or engineered strain of the relevant plant genus from which the lipophilic agent is to be extracted.

For example, for the extraction of astaxanthin, the plant source may be an algae or a microalgae, typically *Haematococcus pluvialis*. In another non-limiting example, lycopene may be extracted from any plant source containing lycopene such as tomatoes, water melon, etc. Another example is extraction of chlorogenic acid from green coffee beans.

Similarly, the process described herein may be used to reduce the content of a non-desired or toxic lipophilic agent (such as gossipol) in a plant-based material, thereby obtaining a purified plant-based material.

In some embodiments, the plant source may be selected from althea, American *ginseng, Berberis* (barberry), belladonna, billberry, borage, catnip, cayenne pepper, Geranium (cranesbill), *Echinacea, Fallopia multiflora* (Fo-Ti), ginger, *Hydrastis canadensis* (goldenseal), *Athyrium* (lady-fern), licorice, cinnamon, coffee beans, marijuana, *Silybum marianum* (milk thistle), parsley, peppermint, rosemary, *Serenoa repens* (saw palmetto), *Scutellaria* (skullcap), *Hypericum perforatum* (st. John's wort), cherries, *Melaleuca* (tea tree), valerian, *Salix alba* (white willow), *Dioscorea* (wild yam), *Hamamelis* (witch hazel), lavender, stevia, agave, vanilla, acai, *Moringo gurana*, aloe, nutmeg, dill, fenugreek, *aronia* (chokeberries), pomegranate, *Salvia hispanica* (chia), *Linum* (flax), *Lycium barbarum, spirulina, Sargassum siliquastrum, Piper nigrum* (black pepper), *Olea europaea* (olive), *Pimenta* (allspice), *Curcuma* (turmeric), carrots, tomatoes, beetroot, *Tagetes* (marigold), and others.

The process of this disclosure may be carried out utilizing any part of the plant source that may contain the desired lipophilic agent; i.e. in some embodiments, the plant source is selected from flowers, inflorescences, buds, fruit, pericarp, seeds, leaves, stems, stalks, bulbs, roots, and any mixture thereof.

The plant source may be provided in any desired form, for example, as a powder, granules, pellets, tablets, shredding, purée, mash, desiccated plant part, or a non-treated plant part (e.g. non-treated leaves, seeds, inflorescence, etc.). The plant source may be provided fresh, dried, freeze-dried, lyophilized, semi-desiccated or desiccated.

The term agent-loaded medium is meant to denote an extraction medium as described herein, into which at least 200 ppm (0.02 wt %) of lipophilic agent is solubilized. In some embodiments, the agent-loaded medium comprises between about 0.02 and 20 wt % of the lipophilic agent. In other embodiments, the agent-loaded medium may comprise between about 0.02 and 15 wt % of lipophilic agent, between about 0.02 and 10 wt % of lipophilic agent, between 0.02 and 5 wt % lipophilic agent, or between about 0.02 and 0.5 wt % of lipophilic agent. In some other embodiments, the agent-loaded medium may comprise between about 0.5 and 20 wt % of lipophilic agent, between about 1 and 20 wt % of lipophilic agent, between 1.5 and 20 wt % lipophilic agent, or between about 2 and 20 wt % of lipophilic agent.

As noted above, the microemulsion used for extraction in the process of this disclosure comprises at least one oil, at least one hydrophilic surfactant and at least one co-surfactant, and optionally comprising at least one co-solvent.

In the context of the present disclosure, the term oil refers to natural or synthetic oil in which the desired lipophilic agent may be solubilized. The oils used in the extraction media of this disclosure may be approved for administration to a subject. In some embodiments, the oil may be selected from essential oils (such as R-limonene, D-limonene, terpenes or terpene-less), mineral oil, paraffinic oils, phospholipids, polar lipids (squalenes, sphingomyelins), waxes, vegetable oils, triglycerides, glycerides, fatty acids and esters of fatty acids, liquid hydrocarbons and others, and any mixture thereof.

According to some embodiments, the oil may be selected from medium-chain triglycerides (MCT), olive oil, soybean oil, canola oil, cotton oil, palmolein, sunflower oil, corn oil, isopropyl myristate, oleyl lactate, coco caprylocaprate, hexyl laurate, oleyl amine, oleic acid, oleyl alcohol, linoleic acid, linoleyl alcohol, ethyl oleate, hexane, heptanes, nonane, decane, dodecane, D-limonene, neem oil, lavender oil, peppermint oil, anise oil, menthol, capsaicin, grape seed oil, pomegranate oil, avocado oil, sesame oil, fish oil, omega oils and omega fatty acids, and similar essential oils and mixtures thereof.

According to other embodiments, the oil is selected from at least one medium-chain triglyceride (MCT), castor oil, R-(+)-Limonene, glycerol, isopropyl myristate, ethyl laurate, olive oil, benzyl alcohol, laurylacetate, lauryl lactate, oleyl lactate, cetyl alcohol, ethyl hexyl laurate, ethyl hexyl oleate, and others.

The oil may be present in the extraction medium, according to some embodiments, at an amount of between about 0.5 and 20 wt %.

The extraction media comprise at least one hydrophilic surfactant. The term hydrophilic surfactant refers to ionic or non-ionic surfactants having a hydrophilic nature, i.e. a surfactant having an affinity for water. Exemplary surfactants are polyoxyethylene sorbitan monolaurate, polyoxyethylene sorbitan monopalmitate, polyoxyethylene sorbitan monooleate, and polyoxyeyhylene esters of saturated and unsaturated castor oil, ethoxylated monglycerol esters, ethoxylated fatty acids, ethoxylated fatty acids of short and medium and long chain fatty acids, and others.

In some embodiments, the at least one hydrophilic surfactant is selected from Solutol HS15 (polyethylene glycol (15)-hydroxystearate), polyoxyethylenes, ethoxylated (20EO) sorbitan mono laurate (T20), ethoxylated (20EO) sorbitan monostearate/palmitate (T60), ethoxylated (20EO) sorbitan mono oleate/linoleate (T80), ethoxylated (20EO) sorbitan trioleate (T85), castor oil ethoxylated (20EP to 40EO); hydrogenated castor oil ethoxylated (20 to 40EO), ethoxylated (5-40 EO) monoglyceride stearate/plamitate, polyoxyl 35 and 40 EOs castor oil. According to other embodiments, the hydrophilic surfactant may be selected from polyoxyl 35 castor oil, polysorbate 40 (Tween 40), polysorbate 60 (Tween 60), polysorbate 80 (Tween 80), Mirj S40, Oleoyl macrogolglycerides, Polyglyceryl-3 dioleate, ethoxylated hydroxyl stearic acid (Solutol HS15), sugar esters (sucrose mono oleate, sucrose mono stearate), polyglycerol esters (10 glycerol mono oleate, 6 glycerol monolaurate, or mono oleate); and soaps such as sodium-, potassium-, ammonium-, ethanol-amine- of a short and medium chain saturated and unsaturated fatty acids (e.g. sodium laurate, sodium oleate, sodium linoleate, sodium linolenate and others). The extraction medium may comprise, by some embodiments, between about 30 and 85 wt % of said hydrophilic surfactant.

The term co-surfactant should be understood to encompass any agent, different from the hydrophilic surfactant, which is capable (together with the hydrophilic surfactant) of lowering the interfacial tension between the oil phase and an aqueous phase to almost zero (or zero) allowing for the formation of a homogeneous mixture and geometrical or physical integration of the agent to the interface or the oily core of the nanostructure. According to some embodiments, the co-surfactant is selected from polyols, diglycerides, polyoxyethylenes, and others.

The co-surfactant may be at least one polyol, i.e. an alcohol containing at least 2 hydroxyl groups, for example ethylene glycol, glycerol, polyethylene glycol, polypropylene glycol, sorbitol, mannitol, lactitol, xylitol and others.

In some embodiments, the co-surfactant may be selected from glycerol, polypropylene glycol, polyethylene glycol, sorbitol, xylitol, PEG 200, PEG 400 and PEG 600. In some embodiments, the co-surfactant is present in the microemulsion at an amount of between about 1 and 50 wt %.

In some embodiments, the extraction medium may further comprise at least one solvent. The term solvent refers to an organic compound, different from the oil, which is miscible in the oil and together therewith forms a homogenous oily phase that dissolves and stabilizes the lipophilic agent. The solvent may, according to some embodiments, be selected from liquid hydrocarbons, alcohols, and others. According to some embodiments, the solvent may be selected from ethanol, propanol, isopropanol, acetic acid, lactic acid, fumaric acid, malic acid, tartaric acid and succinic acid and others. In some embodiments, the solvent may be present in the medium at an amount of between about 0.1 and 25 wt %.

The co-solvent may be a polyol, such as propylene glycol, glycerol, xylitol or short chain alcohols such as ethanol, propanol, iso-propanol and others.

In some embodiments, the extraction medium further comprises at least one phospholipid. Phospholipids such as soy lecithins, rapeseed lecithins, corn or sunflower lecithins, egg lecithins, hydroxylated phospholipids, lyso phospholipids, phosphased phospholipids, hydrogenated phospholipids, Epicorn 200, Phosal 50 PG, dioleyl phosphatidylcholine (DOPC), oleyl palmytoyl phosphatidylcholine (POPC), and the corresponding serines, ethanol amines, glycerol, and others may be used. According to such embodiments, the medium may comprise between about 1 and 10 wt % of phospholipids.

As a man of the art may appreciate, the ratio between the medium's components may be tailored to endow certain characteristics to the medium (such as, desired agent loading, selectivity of extraction, droplet size, viscosity, electrical charge, etc.).

Various active agents are extracted from the plant source by utilizing the extraction medium of the present disclosure. The term extraction or any lingual variation thereof, is meant to denote the transfer of a desired lipophilic agent from the plant source to a solubilizing oily phase of the medium. The process of the present disclosure comprises obtaining a first mixture of a first quantity of the plant source and a first quantity of the extraction medium, for example by mixing. Mixing may be carried out by any suitable known method that does not involve sheer-mixing, for example, manual mixing, magnetically stirring, mixing by pedals, etc.

In some embodiments, the weight ratio (wt/wt) of the first quantity of plant source to the first quantity of medium is between 1:5 and 1:80. In other embodiments, the weight ratio (wt/wt) of the first quantity of plant source to the first quantity of medium may be between 1:7 and 1:70, 1:10 and 1:50, 1:12 and 1:70, or even between 1:15 and 1:60.

In the next stage, the first mixture is homogenized. Homogenization, or any lingual variation thereof, refers to the process of applying sheer forces onto mixtures to break down both the plant source (i.e. reduce the plant source in size) and the extraction medium and blend them to form intimate contact that permits extraction of the lipophilic agent from the plant source into the extraction medium. It is of note that as the systems used in the process of this disclosure have a nanometric size structure, the homogenization has little impact with respect to the micelles size and/or structure of the extraction medium.

In some embodiments, the homogenization (i.e. of step (b)) may be carried out for a period of time of between about 1 minute and about 120 minutes. In other embodiments, the homogenization is carried out for a period of between about 1 minute to 45 minutes, between about 1 minute and 30 minutes, or even between about 1 minute and 20 minutes. In some other embodiments, the homogenization may be carried our between about 5 minutes and about 120 minutes, between about 10 minutes and about 120 minutes, between about 15 minutes and about 120 minutes, or even between about 20 minutes and about 120 minutes.

According to some embodiments, homogenization may be carried out at a pressure of between about 500 and 6,000 psi.

In some embodiments, the homogenization may be carried out at a temperature of between about 5 and about 70° C. In other embodiments, the homogenization may be carried out at a temperature of between about 5 and about 70° C., 10 and about 70° C., 15 and about 70° C., between about 20 and about 70° C., between about 25 and about 70° C., or between about 30 and about 70° C. In some other embodiments, the homogenization may be carried out at a temperature of between about 10 and about 65° C., between about 10 and about 60° C., between about 10 and about 55° C., between about 10 and about 50° C., between about 10 and about 45° C., or even between about 10 and about 40° C. In further embodiments, the homogenization may be carried out at a temperature of between about 15 and about 60° C., between about 20 and about 50° C., or between about 25 and about 45° C.

Homogenization may be carried out by using any suitable type of homogenizer, for example a Silverstone homogenizer, an ultra-torque homogenizer, colloid mill, sonication, ball milling, microfluidizer and other homogenization (or emulsification or dispersion) methods that employ high shear and high mechanical forces or pressure.

Once the mixture has been homogenized, the mixture is separated into a biomass slurry that includes the spent plant source, and an agent-loaded medium. Separating may be carried by any suitable method, for example by filtering through a filter or by centrifugation, decantation or aspiration of the extract phase. In some embodiments, separating the mixture is carried out by centrifugation, which may or may not be followed by filtration.

The plant source may be treated by various pre-treatments prior to extraction, for example chopping, crushing, blending, mashing, pulverizing, lyophilizing, drying, heating, vacuum-treating, freezing, etc. In some embodiments, the plant source is not treated prior to extraction (namely, used as such).

Additional extraction of the lipophilic agent from the biomass slurry may be carried out by employing additional cycles of extraction, thereby maximizing the yield obtained from a given quantity of plant source. Namely, several consecutive extraction cycles may be carried out on the same plant sample by using fresh batches of extraction medium in order to maximize the extraction of the lipophilic agent from the plant source. Thus, in some embodiments, the process may further comprise:

(d) mixing the biomass slurry with a second quantity of extraction medium to obtain a second mixture;
(e) homogenizing the second mixture; and
(f) separating the second mixture into biomass slurry and agent-loaded medium.

After separation into two phases, the agent-loaded medium may be further treated by centrifugation to remove solid particles or liquid droplets having a size of more than 100 nm. Further, the centrifuged material can be filtered via an adequate filter to further reduce presence of particles to obtain clear or almost clear systems. In some embodiments, the desired lipophilic agent can be separate from the loaded medium by any conventional technique, such as cooling (freeze drying or spry-drying), or heating (including vacuum distillation, deodorization etc.), adding anti-solvents or electrolytes, fillers and others.

In some embodiments, the step sequence (d)-(f) is repeated between 1 and 7 times utilizing a given quantity plant source.

In order to obtain a higher lipophilic agent load in the medium, the process may be carried out in several cycles of extraction by using an agent-loaded medium to extract additional lipophilic agent from a fresh sample of plant source (that was not previously extracted). Thus, in some embodiments, the process may further comprise:

(d') mixing the agent-loaded medium with a second quantity of the plant source to obtain a second mixture;
(e') homogenizing the second mixture; and
(f') separating the second mixture into biomass slurry and highly agent-loaded medium.

In some embodiments, the step sequence (d')-(f') is repeated between 1 and 7 times utilizing the same agent-loaded medium.

The mixing, homogenizing and separating parameters of steps (d)-(f) or (d')-(f') may be the same or different than those describe hereinabove in connection with steps (a)-(c).

In both process sequences described herein, it is contemplated by some embodiments that fresh extraction medium and agent-loaded medium are used in different cycles of the process. Namely, some of the cycles may be carried out with fresh extraction medium, while other cycles in the same process sequence may be carried out with agent-loaded medium.

The spent biomass can be further processed by any desirable method to extract further desired components or other lipophilic agents, by any suitable means or by using a tailored extraction medium to extract the additional desired component(s).

Agent-loaded medium quotas from different extraction batches may be mixed together to obtain a desired concentration of the lipophilic agent in a final product. Such mixing may be carried out by any suitable mixing method. The agent-loaded medium can be used as-is, or can be further formulated by addition of other components to be loaded into liquid-gel capsules, creams, gels, patches, etc. as further detailed below.

In another aspect of this disclosure, there is provided an extraction medium for extraction of a lipophilic agent from a plant source containing said lipophilic agent, comprising at least one oil, at least one hydrophilic surfactant, and at least one co-surfactant, the microemulsion optionally further comprising at least one phospholipid, at least one solvent, and/or at least one co-solvent.

In a further aspect, this disclosure provides an agent-loaded medium obtained by the process described herein.

Yet a further aspect of this disclosure provides an agent-loaded medium comprising at least 200 ppm (0.02 wt %) of a desired lipophilic agent, at least one oil, at least one hydrophilic surfactant, and at least one co-surfactant, the agent-loaded medium optionally further comprising at least one solvent, at least one co-solvent, and/or at least one phospholipid.

The oil, hydrophilic surfactant, solvent, co-solvent and phospholipid are selected from those described hereinabove.

In additional embodiments, each of the mediums described herein may additionally comprise at least one additive, selected from antioxidants (tocopherols), oxygen scavengers, preservatives, membrane-piercing agents, trans-membrane penetrating enhancers (e.g. transcutol, isosorbide, oleic acid, monoglycerides of fatty acids propylene glycol, maltodextrines, cyclodextrines, etc).

As noted above, the agent-loaded media may be used as is, i.e. without addition of other components, as food stuff, food supplement, nutritional or pharmaceutical compositions. Alternatively, the agent-loaded media of this disclosure may be formulated into various formulations, by diluting them with various diluents or by incorporating them into various other carriers. The concentrate, as well as the diluted media of this disclosure, greatly increases the stability of the formulation over time, reduces the risk of contamination, broadens the scope of its application to a great variety of concentrations (various dose) and diluted forms, while permitting the medical professionals the decision how, when and which formulation to prepare prior to use.

The term concentrate denotes a substantially water-free (up to 10 wt % water), oil-based structured lipid/surfactants system, in which surfactant tails are solubilized by the lipophilic agent and the oil facilitating full dilution by a diluent aqueous phase (are dilutable) at will to form diluted media for any desired application. In other words, the concentrates are designed for fast and quantitative dilution in a suitable diluent, for example water for injection, saline, and aqueous solutions (such as sugar and sweetener solutions and water-alcohol mixtures), forming the diluted media, as will now be described. Upon dilution with a suitable diluent, the concentrate of the invention spontaneously forms clear homogeneous microemulsions, which are at first "solvated domains (or clusters) of surfactant" meso-phases that upon minor dilution (ca. 20-30 wt %) form water-in oil nanodroplets; and upon further dilution transform to bicontinuous mesophases and into oil-in-water (O/W) nanodroplets, in which the diluent forms the continuous phase, while the oil phase is in the form of discrete droplets of nanometric size (i.e. the diluted mediums or diluted microemulsions). As noted above, the diluted media are formed from the concentrate spontaneously, namely without the need to apply any shear, cavitation or homogenization processes.

In addition to providing flexibility in formulating and better control of the lipophilic agent administration dose, the concentrates produced by the process described herein are substantially free, i.e. devoid, of water. Once water is absent from the medium, the concentrates lack the environment sustaining microorganisms growth (e.g. fungi or bacteria), permitting longer storage without (or with minimal) risk of contamination. Without wishing to be bound by theory, one of the reasons due to which almost no bacterial contamination is observed for such concentrates may be the absence of unbound water, thereby limiting microbial growth and substantially extending the shelf life of the agent-loaded medium.

In some embodiments, the agent-loaded media (i.e. concentrates) are entirely devoid of water. In other embodiments, the agent-loaded media (concentrates) contain up to 10 wt % water.

The ratio between the concentrate and the diluent depends on the desired final concentration of lipophilic agent in the formulation. According to some embodiments, the diluted medium comprises between about 2 and about 98 wt % of the diluent.

In another aspect, the present disclosure provides a food, food supplement, fragrance formulation, pharmaceutical or nutraceutical composition comprising the agent-loaded media as described herein.

In some embodiments, the pharmaceutical composition may comprise at least one pharmaceutically acceptable carrier. The "pharmaceutically acceptable carriers" described herein, for example, vehicles, adjuvants, excipients, or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the lipophilic agent, as well as by the particular method used to administer the composition. Accordingly, there is a wide variety of suitable formulations of the pharmaceutical composition of the present disclosure.

As described above, when diluted with an aqueous liquid, a spontaneous oil-in-water (O/W) microemulsion is formed, in which the diluent forms the continuous phase, while the oil phase is in the form of discrete droplets of nanometric size. In some embodiments, the oil droplets of the diluted medium may have an average droplet diameter of at less than 100 nanometers.

In some other embodiments, the droplets size is between about 10 and 30 nm (nanometers). The droplet size refers to the arithmetic mean of measured droplets' diameters, wherein the diameters range ±15% from the mean value.

Further, diluted media (i.e. O/W microemulsions) of the present disclosure are characterized by a mono-disperse size distribution of the oil droplets. Namely, the size distribution of the oil droplets is narrow, without significant divergence from the mean size value. In some embodiments, the polydispersity index (PDI) of the distribution of oil droplets is between about 0.03 and 0.1.

The aqueous diluent may be selected from water, water for injection, saline, dextrose solution, or a buffer having a pH between 3 and 9 or any other isotonic solution.

The lipophilic agent is stably contained (i.e. solubilized) within the oil droplets, and is controllably released into the blood stream after administration. Without wishing to be bound by theory, the agent-oil-surfactant system forms strong molecular interactions, thus permitting solubilization of the lipophilic agent within the oil droplets of the microemulsion. Upon high dilutions, i.e. when introduced into the blood stream, a micellar system is formed, thereby enabling (because of its dynamic structure) the release of the lipophilic agent to obtain the desired effect via simple diffusion.

The pharmaceutical composition may comprise a variety of additional components, depending on the administration route and/or desired properties of the formulation, such as aqueous and non-aqueous diluents, isotonic sterile injection solutions, anti-oxidants, buffers, bacteriostats, suspending agents, solubilizers, thickening agents, gelling agent, emollients, moisturizers, stabilizers, preservatives, buffers, coloring agents, a fragrance, absorbers, filters, electrolytes, proteins, chelating agents, and others.

In some embodiments, the pharmaceutical composition is in a form selected from a gel, a lotion, oil, soap, a spray, an emulsion, a cream, an ointment, capsules, soft-gel capsules, chewing gum, a patch, or a solution.

In other embodiments, the formulation may be adapted for delivery of the lipophilic agent in various routes of administration, including topical, oral, rectal, vaginal, transdermal, subcutaneous, intravenous, intramuscular, intranasal, by inhalation, occularly or parenterally into the circulatory system of a subject.

Formulations suitable for oral administration can consist of (a) liquid solutions, such as an effective amount of the compound, or composition comprising same, dissolved in diluents, such as water, saline, or juice (e.g. orange juice); (b) capsules, sachets, tablets, lozenges, and troches, each containing a predetermined amount of the active ingredient, as solids or granules; (c) powders; (d) suspensions in an appropriate liquid; and (e) concentrates or diluted microemulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active formulation in an inert base, such as gelatin and glycerin, or sucrose and acacia, emulsions, gels, and the like containing, in addition to the active formulation, such carriers as are known in the art.

Another aspect of this disclosure provides an agent-loaded medium (either in concentrate or diluted form) or a pharmaceutical composition of this disclosure, for use in treating a condition selected from pain associated disorders (as an analgesic), inflammatory disorders and conditions (as anti-inflammatory), apatite suppression or stimulation (as anoretic or stimulant), symptoms of vomiting and nausea (as antiemetic), intestine and bowl disorders, disorders and conditions associated with anxiety (as anxiolytic), disorders and conditions associated with psychosis (as antipsychotic), disorders and conditions associated with seizures and/or convulsions (as antiepileptic or antispasmodic), sleep disorders and conditions (as anti-insomniac), disorders and conditions which require treatment by immunosuppression, disorders and conditions associated with elevated blood glucose levels (as antidiabetic), disorders and conditions associated with nerve system degradation (as neuroprotectant), inflammatory skin disorders and conditions (such as psoriasis), disorders and conditions associated with artery blockage (as anti-ischemic), disorders and conditions associated with bacterial infections, disorders and conditions associated with fungal infections, proliferative disorders and conditions, disorders and conditions associated with inhibited bone growth, and others.

A further aspect, provides a method of treating a subject suffering from a condition, the method comprising administering to the subject an effective amount of the agent-loaded medium (either in concentrate or diluted form) or the pharmaceutical composition of this disclosure.

In some embodiments, the condition may be selected from those described hereinabove.

The agent-loaded media produced by the process described herein may be used as such to induce at least one effect, e.g. therapeutic effect, or may be associated with at least one agent, e.g. therapeutic agent, which is capable of inducing, enhancing, arresting or diminishing at least one effect, by way of treatment or prevention of unwanted conditions or diseases in a subject. The at least one agent (substance, molecule, element, compound, entity, or a combination thereof) may be selected amongst therapeutic agents, i.e. agents capable of inducing or modulating a therapeutic effect when administered in a therapeutically effective amount, and non-therapeutic agents, i.e. which by themselves do not induce or modulate a therapeutic effect but which may endow the pharmaceutical composition with a selected desired characteristic.

The pharmaceutical compositions of the present disclosure may be selected to treat, prevent or ameliorate a pathology or condition. The term treatment or any lingual variation thereof, as used herein, refers to the administering of a therapeutic amount of the composition or system described herein, whether in a concentrate form or in a diluted microemulsion form, which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above.

As known, the effective amount for purposes herein may be determined by such considerations as known in the art. The effective amount is typically determined in appropriately designed clinical trials (dose range studies) and the person versed in the art will know how to properly conduct such trials in order to determine the effective amount. As generally known, the effective amount depends on a variety of factors including the distribution profile within the body, a variety of pharmacological parameters such as half-life in the body, on undesired side effects, if any, on factors such as age and gender, and others.

The term subject refers to a mammal, human or non-human.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between. It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

As used herein, the term about is meant to encompass deviation of ±10% from the specifically mentioned value of a parameter, such as temperature, pressure, concentration, etc.

FIGS. 9A-9B show various agent-loaded mediums, concentrates (FIG. 9A) and diluted by 90 wt % water (FIG. 9B), from left to right: unloaded AX-1, carrots, turmeric, marigold, beetroot, nutmeg, tomato, black pepper, allspice and olive leaves.

FIGS. 10A-10B show the concentration (FIG. 10A) and yield of extraction (FIG. 10B) of astaxanthin, curcumin and piperine as a function of the number of extraction cycles.

DETAILED DESCRIPTION OF EMBODIMENTS

Astaxanthin as a Model Lipophilic Agent

In the following examples, astaxanthin (AX) was used as a model lipophilic agent. Astaxanthin is a water-insoluble antioxidant from the carotenoids group, having the following structure (Formula I):

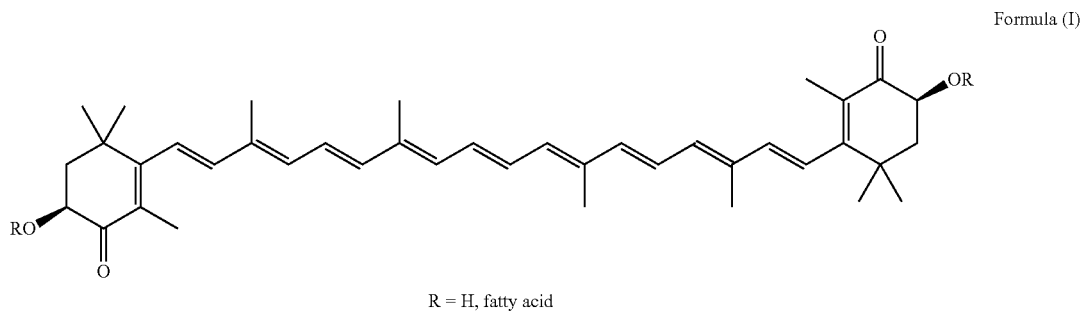

R = H, fatty acid

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

It is to be understood that various other lipophilic agents may be extracted from various plant sources by the process and extraction media disclosed herein, and the extraction of astaxanthin is brought for exemplifying purposes only. Some additional exemplary lipophilic agents will be provided below.

Extraction Medium Composition and Preparation

As noted above, the extraction media used for the extraction process are self-assembled systems which are formed in a spontaneous manner. Therefore, the compositions of the extraction medium were prepared by simple mixing of ingredients at 15-70° C. An exemplary process for preparing the extraction medium involves mixing together the oil, the surfactant and the co-surfactant (and where applicable also a solvent, a co-solvent and/or a phospholipid) until a homogenous, clear (transparent) mixture is obtained. In case the surfactants or oil are solid at room temperature, heating can be applied while mixing to allow full dissolution and formation of the empty extraction medium.

The extraction medium is then slowly added to the plant to allow appropriate wetting and then mixed and homogenized. Another variation of the process includes adding solid plant parts (for example leaves or buds) stepwise to the empty (un-loaded) extraction medium until a homogeneous slurry is obtained.

Extraction was carried out under heating and inert atmosphere, thereby solubilizing the desired lipophilic agent into the extraction medium. The mixture was allowed to settle to the bottom of the mixing vessel before filtration and/or centrifugation.

Table 1 provides details of exemplary formulations used in the process of the present disclosure.

TABLE 1

Formulations of extraction medium

| | Formulation AX-1 | | Formulation AX-2 | |
|---|---|---|---|---|
| | Component | wt % | Component | wt % |
| Oil | R-(+)-Limonene | 5 | MCT | 3.5 |
| Hydrophilic surfactant | Polysorbate 80 (Tween 80) | 45 | Tween 80 | 35 |
| | | | Chremophore | 42 |
| Co-surfactant | Propylene glycol (PG) | 45 | PG | 13 |
| Solvent | Ethanol | 5 | Ethanol | 1.5 |

Extraction Process Parameters
Effect of Plant-to-Medium Ratio

*Haematococcus pluvialis* microalgae samples provided by Algatech (batch number 219) were mixed with AX-1 extraction medium at a weight ratio of between 1:3 and 1:15 (plant:medium). The mixture was then homogenized at room temperature using lab Silverson homogenizer L5M-A for 30 minutes. After homogenization, each sample was centrifuged at 4000 rpm for 20 minutes or filtered through cotton wool. Samples were prepared in triplicates.

Analysis of astaxanthin content in the extracts was carried out by UV-vis spectrophotometer (max value at 472 nm) or HPLC vis-à-vis a calibration curve (using the following conditions: C18 column, mobile phase gradient of methanol/water (69/31 v/v %) to 100% methanol, flow rate 0.3 ml/min).

Figure 1A:
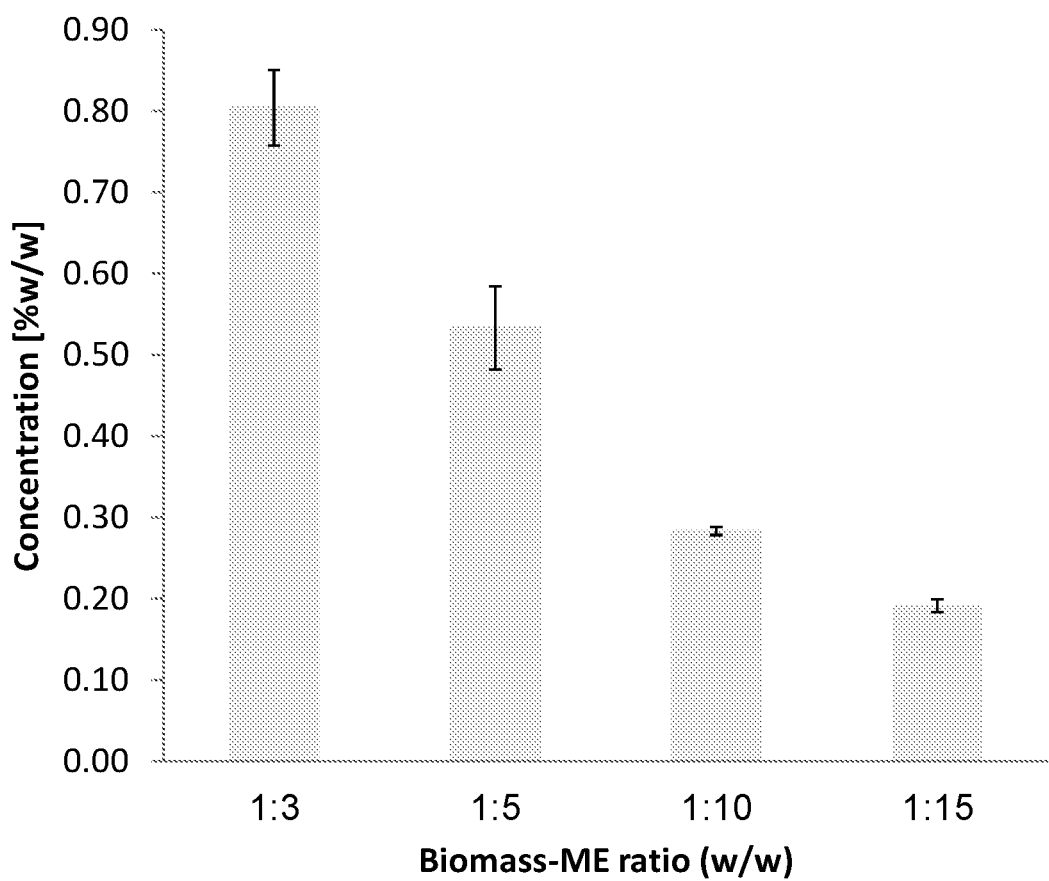
FIGS. 1A-1B show astaxanthin (AX) concentration (FIG. 1A) and yield of AX extraction (FIG. 1B) in the AX-1 extraction medium as a function of plant-to-medium ratio (w/w).
Figure 1B:
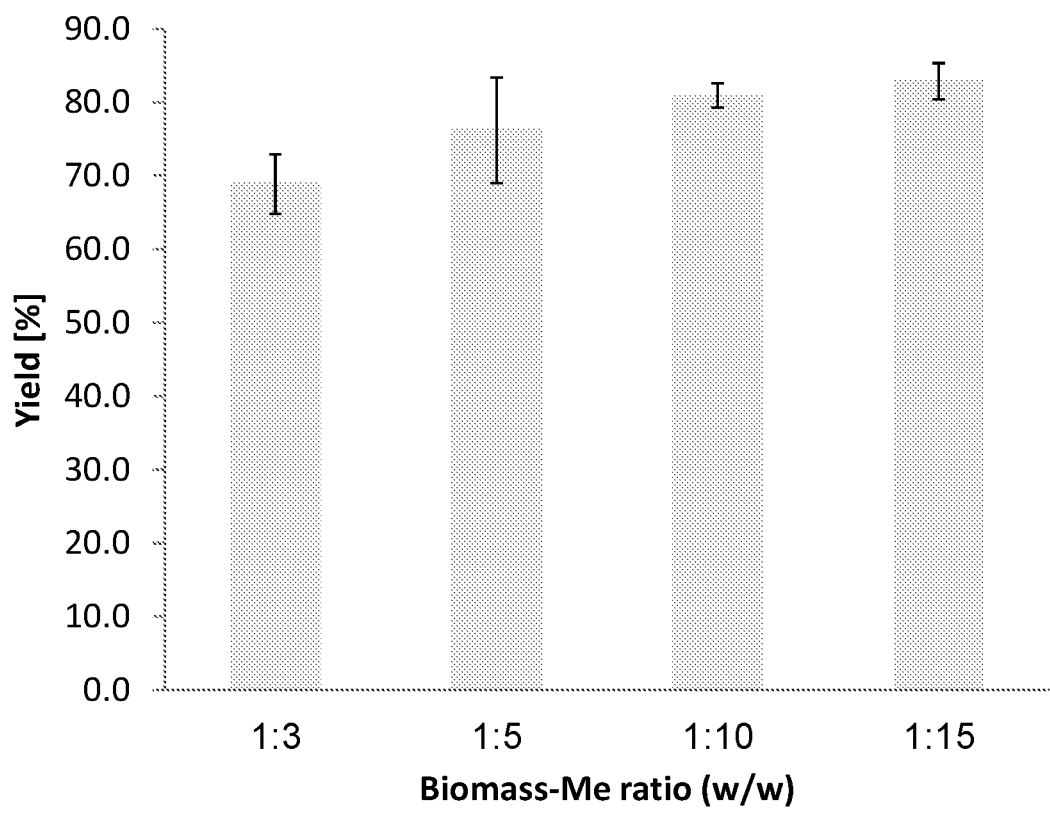

FIGS. 1A-1B show the concentration of astaxanthin (AX) in the extracts and the extraction yield, respectively, as a function of the plant-to-medium ratio. Although the nominal concentration decreases upon increasing the plant:medium ratio (i.e. due to the dilution effect), the higher the weight ratio between the medium and the microalgae a higher extraction yield is obtained, reaching app. 80% extraction yield in a single extraction cycle.

Effect of Extraction Duration

*Haematococcus pluvialis* microalgae samples were mixed with AX-1 extraction medium at a weight ratio of 1:40. The mixture was then homogenized at room temperature using Silverson homogenizer for various periods of time. After homogenization, each sample was centrifuged at 4000 rpm for 20 minutes or filtered through cotton wool. Samples were prepared in triplicates.

Figure 2A:
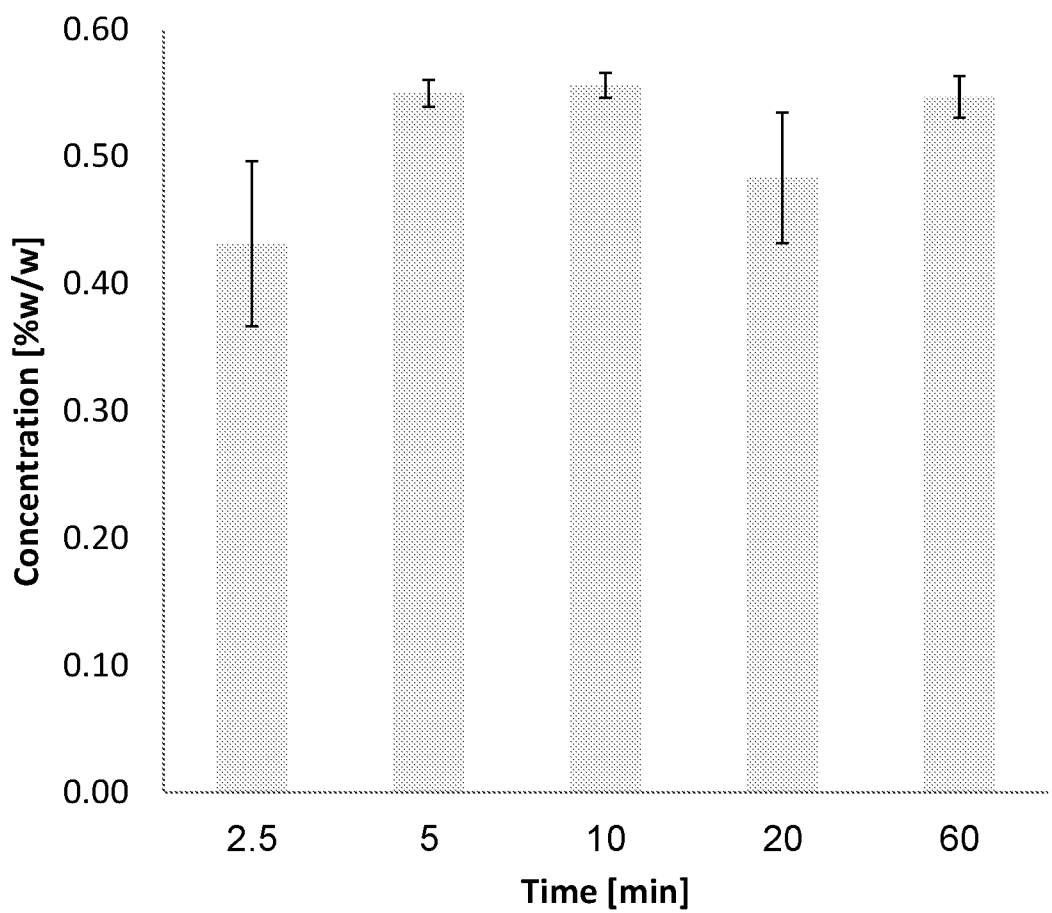
FIGS. 2A-2B show AX concentration (FIG. 2A) and yield of AX extraction (FIG. 2B) in the AX-1 extraction medium as a function of extraction duration.
Figure 2B:
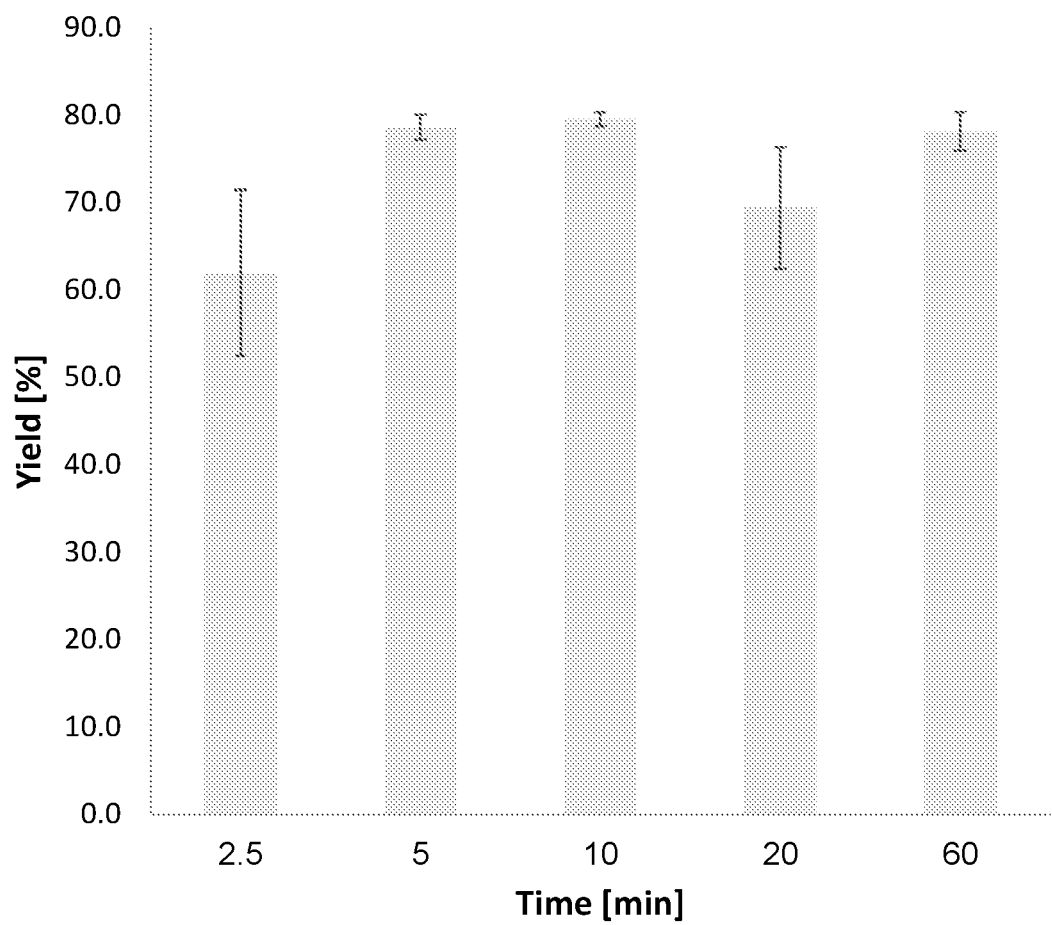

Analysis of astaxanthin content in the extracts was carried out by UV-vis spectrophotometer (max value at 472 nm) or HPLC vis-à-vis calibration curves. FIGS. 2A-2B show the concentration of AX in the extracts and the extraction yield, respectively, as a function of the extraction time.

As can clearly see from the results, extraction yields of AX in a single extraction round ranged between 60-80% and up to ~0.6 wt % AX-loading in to the medium.

Multiple-Extractions Processes
Multiple Cycles Using the Same Quota of Extraction Medium Increasing the concentration of the lipophilic agent, in this case AX, in the medium was carried out by a multi-extraction process. For the multi-extraction process a number of extraction cycles are carried out by using the same quota of medium for several consecutive extraction cycles, in each cycle a fresh sample of microalgae is extracted according to the following procedure.

A *Haematococcus pluvialis* microalgae biomass sample was mixed with AX-1 extraction medium at a weight ratio of 1:10. The mixture was then homogenized at room temperature using Silverson homogenizer for 10 minutes. After homogenization, each sample was centrifuged at 4000 rpm for 20 minutes or filtered through cotton wool. After separating the AX-loaded medium from the spent biomass, the AX-loaded medium was weighed and a new sample of microalgae was added at a weight ratio of 1:15 (plant:medium). Homogenization and separation were carried out for the new mixture. One additional cycle of extraction was carried out, amounting to a total of 3 extraction cycles.

Samples of the medium were taken in between cycles to assess the effect of the number of cycles on the AX-loading of the medium.

Figure 3A:
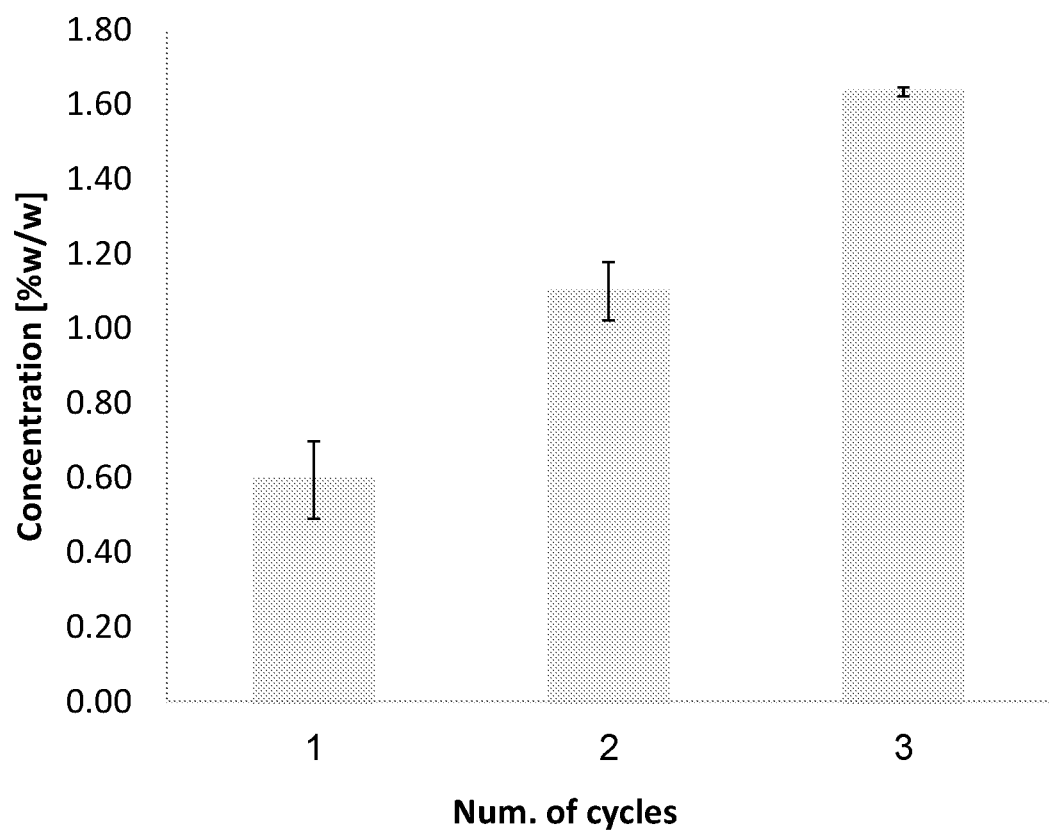
FIGS. 3A-3B show AX concentration (FIG. 3A) and yield of AX extraction (FIG. 3B) in the AX-1 extraction medium as a function of the number of extraction cycles.
Figure 3B:
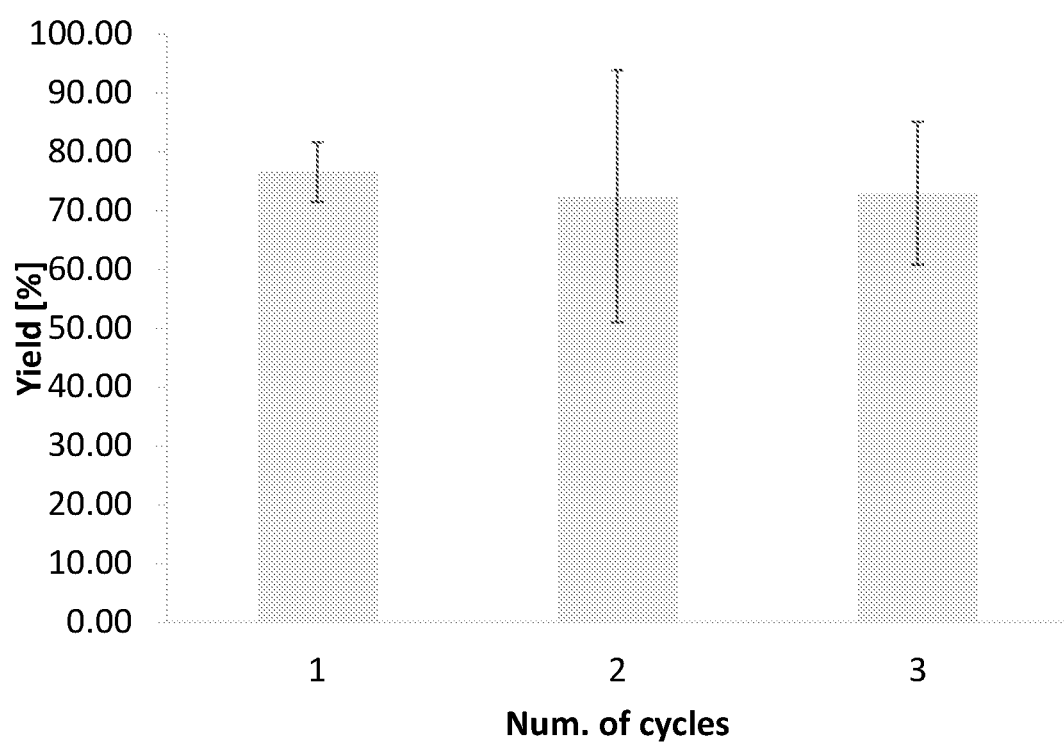

Analysis of AX content was done according to the description hereinabove. FIGS. 3A and 3B show the concentration of AX in the extracts and the extraction yield, respectively, as a function of the number of extraction cycles.

As evident from the results, the AX content in the medium increases by at least 2.5-folds as a result of the multi-extraction process. However, as the extraction medium becomes loaded with AX, the extraction efficiency (i.e. yield) of the medium decreases compared to the extraction efficiency at the first cycle of extraction, due to the proximity of the AX content to the maximum loading capacity of the medium.

Multiple Cycles Using the Same Biomass of Microalgae

Similarly, the efficiency of extraction from the plant source by using multiple cycles of extraction from the same biomass was tested; namely, the capability to utilized spent biomass for extraction of additional AX from the same sample.

A *Haematococcus pluvialis* microalgae biomass sample was mixed with AX-1 extraction medium at a weight ratio of 1:10. The mixture was then homogenized at room temperature using Silverson homogenizer for 10 minutes. After homogenization, each sample was centrifuged at 4000 rpm for 20 minutes or filtered through cotton wool. After separating the AX-loaded medium from the spent biomass, the spent biomass was weighed and a fresh quota of extraction medium was added at a weight ratio of 1:15 (plant:medium). Homogenization and separation were carried out for the new mixture. One additional cycle of extraction was carried out, amounting to a total of 3 extraction cycles.

Samples of the medium were taken in between cycles to assess the effect of the number of cycles on the AX-loading of the medium.

Figure 4A:
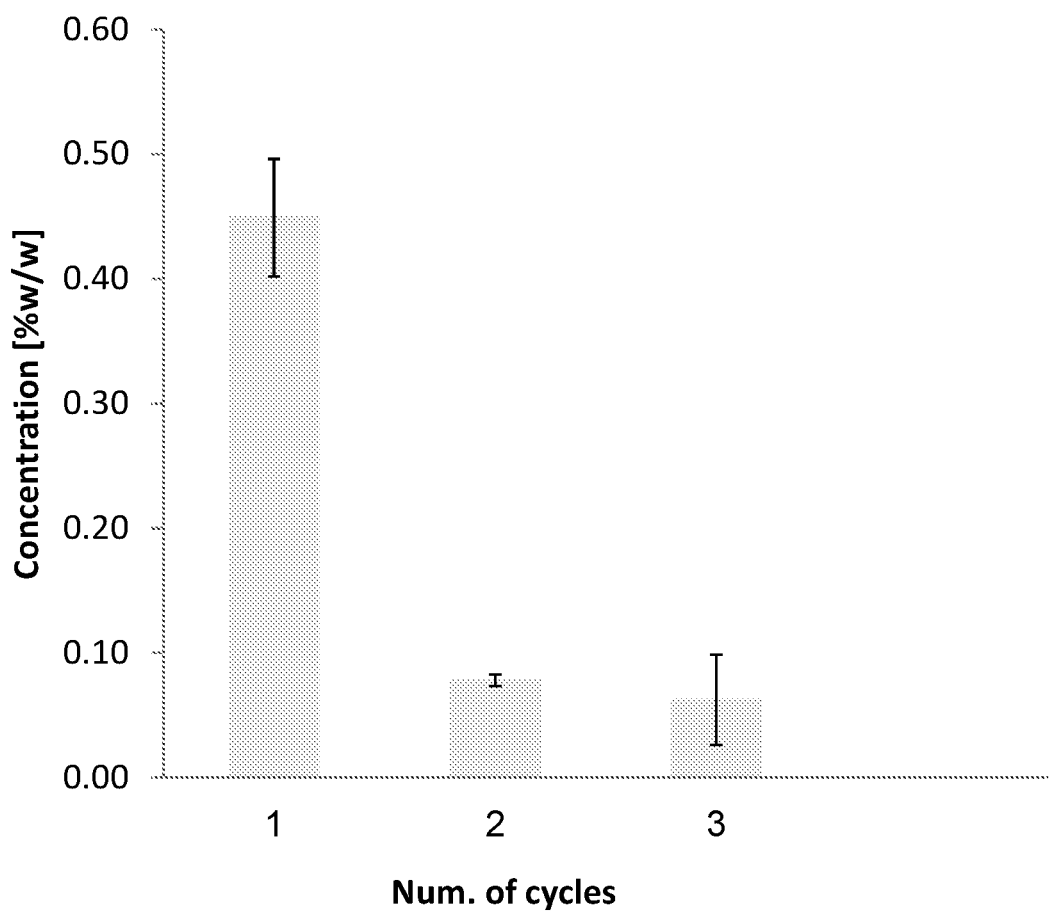
FIGS. 4A-4B show AX concentration (FIG. 4A) and yield of AX extraction (FIG. 4B) in the AX-1 extraction medium as a function of the number of extraction cycles from the same biomass.
Figure 4B:
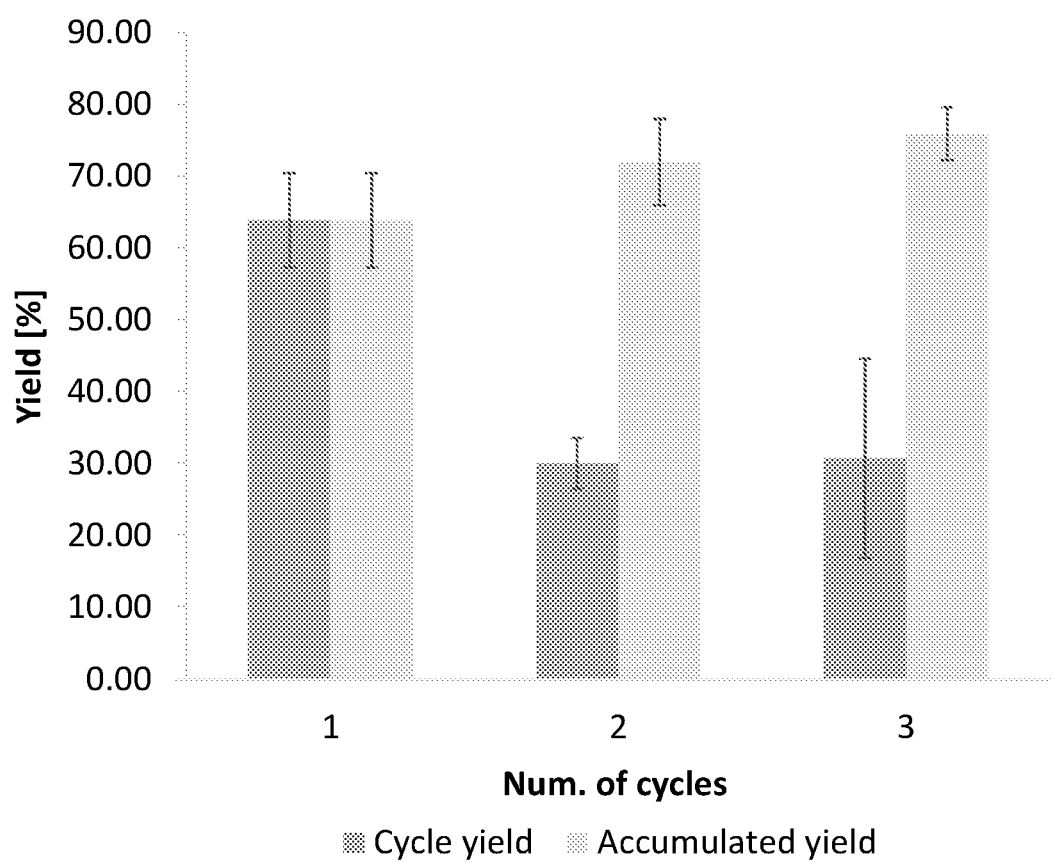

Analysis of AX content was done according to the description hereinabove. FIGS. 4A and 4B show the concentration of AX in the extracts and the extraction yield, respectively, as a function of the number of extraction cycles.

As can clearly be seen, the extraction of AX from the microalgae in the first extraction cycle is shown to have relatively high extraction yield. Namely, in the second and third cycles of extraction from the same sample of microalgae (i.e. extraction of the spent biomass by fresh extraction medium quota), significantly less AX was extracted from the spent biomass. This attests to the relatively high extraction yield obtained in the first extraction round (namely when extracting the fresh microalgae).

However, as also evident, it is possible to reach about 80% extraction yield cumulatively by employing multiple extraction cycles on the same spent biomass.

Tables 2-3 below provide a comparative summary of the extraction yields by using the various extraction processes.

TABLE 2 extraction yields of a single extraction cycle

| Extraction duration | AX conc. in ME (wt %) | Extraction yield (%) |
|---|---|---|
| 10 min | 0.56 ± 0.01 | 79.5 ± 0.8 |
| 60 min | 0.55 ± 0.02 | 79.5 ± 0.8 |

TABLE 3 extraction yields of multiple extraction cycles

| | AX conc. in medium (wt %) | | | Extraction yield (%) | | | Accumulated yield (%) |
|---|---|---|---|---|---|---|---|
| | $1^{st}$ cycle | $2^{nd}$ cycle | $3^{rd}$ cycle | $1^{st}$ cycle | $2^{nd}$ cycle | $3^{rd}$ cycle | |
| (1) | 0.59 ± 0.01 | 1.10 ± 0.08 | 1.63 ± 0.01 | 76.4 ± 5.1 | 72.4 ± 21.4 | 72.9 ± 12.1 | 73.9 ± 12.9 |
| (2) | 0.45 ± 0.05 | 0.08 ± 0.01 | 0.06 ± 0.04 | 63.8 ± 6.6 | 30.7 ± 03.7 | 31.8 ± 14.8 | 75.9 ± 3.2 |

(1) same medium, new biomass
(2) same biomass, fresh extraction medium

Characterization and Dilutability of the AX-Loaded Medium

Effect of Dilution on the Medium's Structure

As noted above, the media described herein are substantially devoid of water (i.e. in the form of a concentrate), constituted by self-assembled oil-solvated clusters or short domains of surfactants, which differ from the classical reverse micelles. The concentrates are dilutable by any suitable diluent, for example by water, to form a diluted delivery system.

Figure 5:
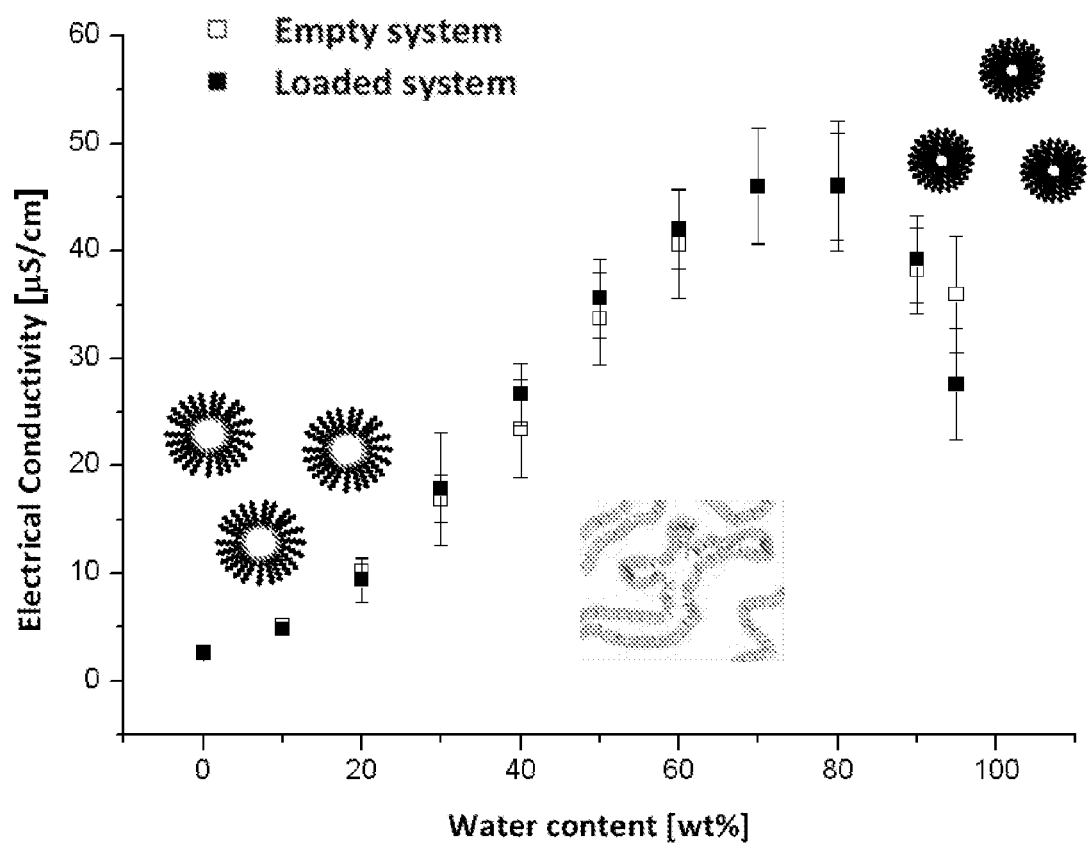
FIG. 5 shows the effect of water dilution on unloaded and AX-loaded extraction medium, as measured by electrical conductivity tests.

The effect of water dilution on the medium's structure was investigated by using electrical conductivity tests. Electrical conductivity measurements were performed at 25±2° C. using a conductivity meter, type CDM 730 (Mettler Toledo GmbH, Greifensee, Switzerland). Measurements were made on empty and AX-loaded samples upon dilution with water up to 95 wt %. No electrolytes were added to the samples. The conductivity allows to distinguish between the continuous phase and the inner phase. The results are shown in FIG. 5.

As can be seen, the microemulsions undergo 2 phase transitions upon increasing the amount of diluent. When in concentrate form, the system is in the form of reverse micelles, solubilizing the AX within the core of the micelle. When mixed with small amounts of water, a bicontinuous structure of solvated (oil-rich) and hydrated (water-rich) domains are formed; upon further dilution with water, the bicontinuous structure progressively and continuously transforms into oil-in-water (O/W) nanodroplets entrapping AX molecules within their oily core (or within the surfactants tails). As also noted above, the transformation to O/W microemulsions is spontaneous, i.e. without the need to employ shear stresses or excessive heating conditions. Thus, throughout the phase transformations occurring upon dilution, AX is stabilized and solubilized within the oily phase (as will be further explained below in connection with SD-NMR analysis).

In addition, when comparing the unloaded system with the AX-loaded system, it seems that the presence of AX has no significant effect on the system's structure and its ability to undergo the phase transitions.

Figure 6:
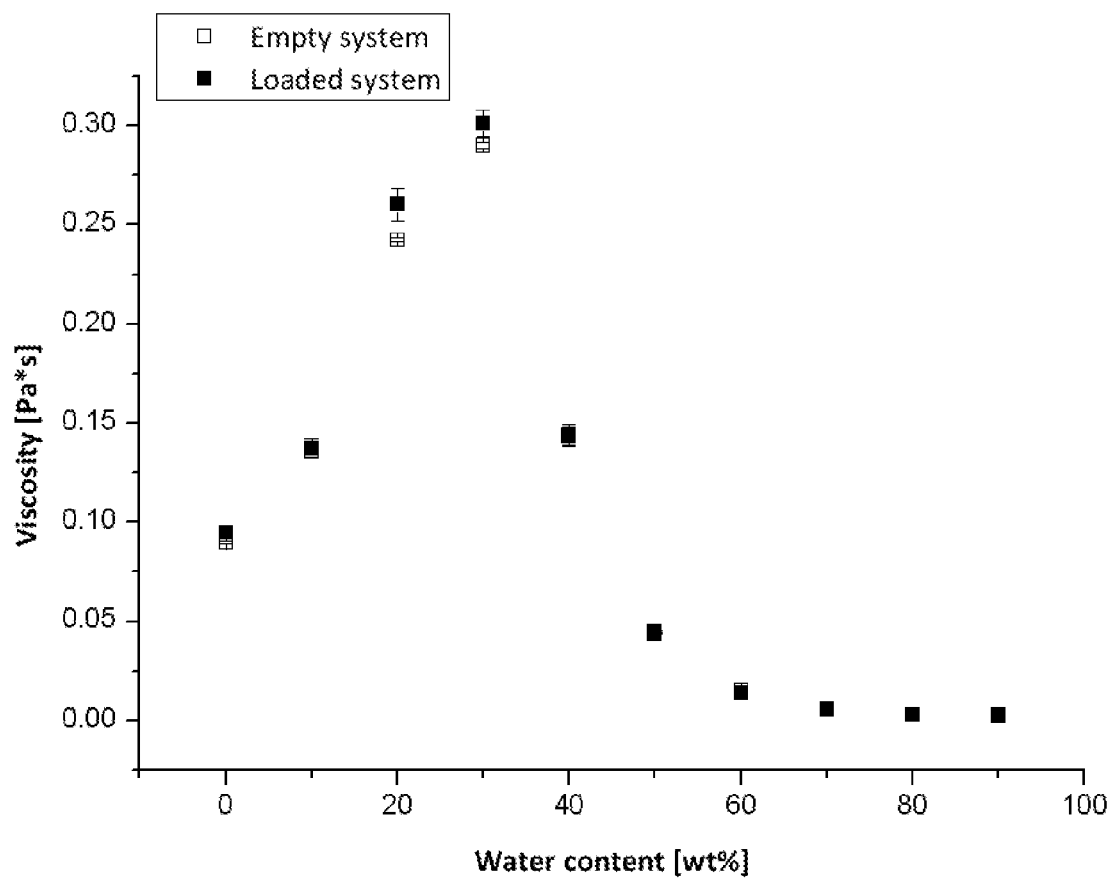
FIG. 6 shows the effect of water dilution on the viscosity of unloaded and AX-loaded extraction medium.

Similar results were obtained in viscosity measurements of unloaded and AX-loaded medium, as shown in FIG. 6. Viscosity measurements were performed at 25±1° C. on empty and AX-loaded MEs (Thermo Electron GmbH, Karlsruhe, Germany) using a cone (60 mm diameter) and glass plate. Shear rates were 0-1000 in the water.

Droplet Size

One of the advantages of the concentrates described herein is the ability to be diluted at various dilution ratios, without significantly affecting the formulation's properties.

The hydrodynamic radius of the oil droplets was measured at room temperature by small-angle x-ray scattering (SAXS). Scattering experiments were performed using CuKα radiation (λ=0.154 nm) from Rigaku RA-MicroMax 007 HF X-ray generator operated at a power rating up to 1.2 kW and generating a 70×70 μm² focal spot. The osmic CMF12-100CU8 unit produced a beam size at the sample position of 0.7×0.7 mm². The scatter radiation passed through a He-filled flight path and was detected by a Mar345 imagine plate detector from Marresearch (Nordestedt, Germany). Samples were inserted into 1.5 mm quartz capillaries and scanned for 15 min at T=25±1° C. The sample to detector distance was calibrated using silver behenate. Curve fitting of the SAXS profiles was performed using Origin (MicroCal, MA).

Average droplet sizes for unloaded and AX-loaded media at different dilutions (i.e. different water concentrations) are provided in Table 4.

TABLE 4

Average droplet size values at different dilutions

| Water content (wt %) | Unloaded system (nm) | AX-loaded (nm) |
|---|---|---|
| 0 | 12.57 | 15.65 |
| 10 | 7.34 | 8.89 |
| 30 | 8.51 | 9.16 |
| 50 | 9.59 | 10.60 |
| 90 | 5.93 | 6.95 |

As clearly evident from Table 4, the droplet sizes of the empty system are smaller than those measured for the loaded systems indicating that AX is located within the core/interface of the drop increasing its size (see also SD-NMR analysis below).

Figure 7:
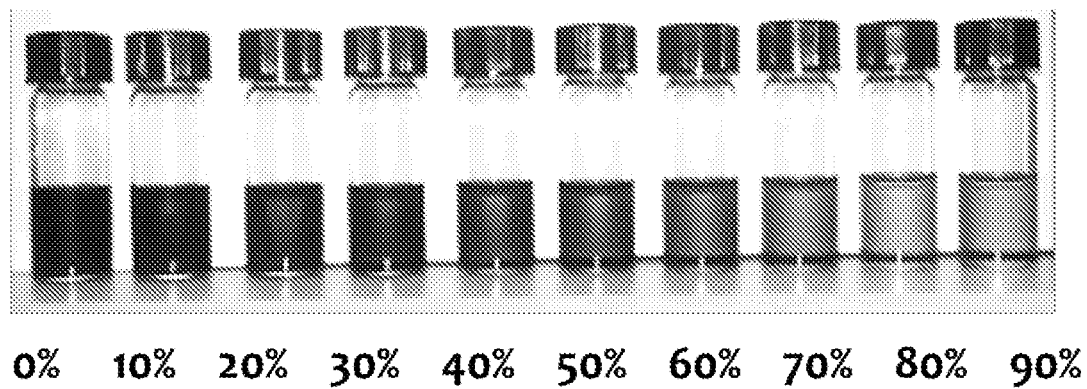
FIG. 7 shows AX-loaded extraction medium, diluted by water (0-90 wt % water).

Further, as seen in FIG. 7, the very small droplet size that characterizes the media described herein (typically have an average droplet diameter of less than 20 nm) enables obtaining clear and transparent microemulsions for prolonged periods of time, without phase separation. The transparency also enables detection of undesired contaminants, thereby allowing the user to easily identify in a visual manner contaminated formulations that are unsuitable for use.

Self-Diffusion NMR (SD-NMR)

In order to determine the structure of the oil droplets (or micelles) of the medium, self-diffusion NMR analysis was carried out. SD-NMR is able to locate each component within the medium via measurements of its diffusion coefficient. Rapid diffusion (>100×10$^{-12}$ m$^2$s$^{-1}$) is characteristic of small molecules, free in solution, while slow diffusion coefficients (<0.1×10$^{-12}$ m$^2$s$^{-1}$) suggest low mobility of macromolecules or bound/aggregated molecules.

NMR measurements were performed with a Bruker AVII 500 spectrometer equipped with GREAT 1/10 gradients, a 5 mm BBO and a 5 mm BBI probe, both with a z-gradient coil and with a maximum gradient strength of 0.509 and 0.544 Tm$^{-1}$, respectively. Diffusion was measured using an asymmetric bipolar longitudinal eddy-current delay (bpLED) experiment, or an asymmetric bipolar stimulated echo (known as one-shot) experiment with convection compensation and an asymmetry factor of 20%, ramping the strongest gradient from 2% to 95% of maximum strength in 32 steps. The spectrum was processed with the Bruker TOPSPIN software. NMR spectra were recorded at 25±0.2° C. The components were identified by their chemical shift in 1H NMR.

Figure 8A:
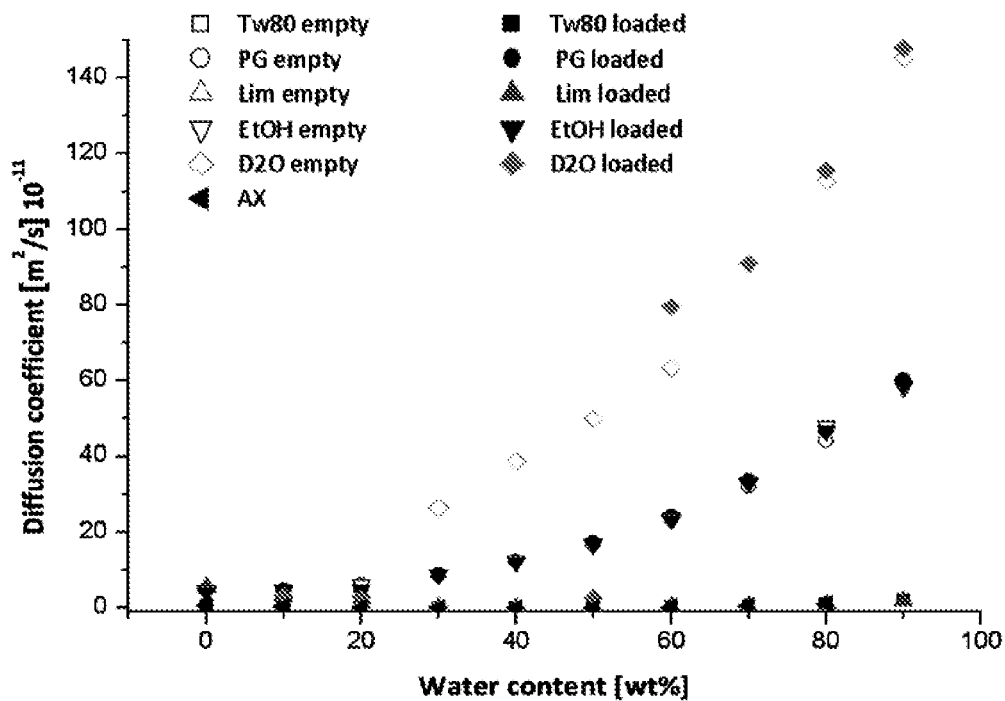
FIGS. 8A-8B show the diffusion coefficients of the components of the extraction medium (as measured by SD-NMR) for unloaded and AX-loaded AX-1 medium: full composition (FIG. 8A), AX-limonene-tween in isolation (FIG. 8B).
Figure 8B:
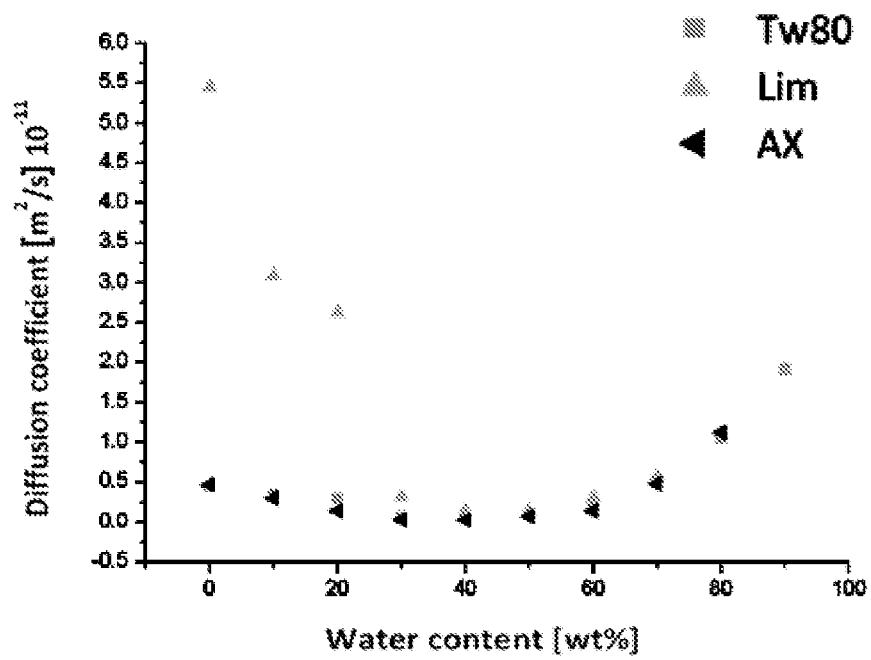

Tables 5-1 and 5-2 shows the diffusion coefficients (Dx, m$^2$/sec) of the unloaded and AX-loaded medium (with 0.5 wt % of AX), respectively, at various water dilutions. The results are also graphically presented in FIGS. 8A-8B.

no free AX is within the aqueous continuous phase, attesting to the ability of the medium to contain and stabilize AX.

Further, at dilutions of ~30-50% water, AX binds water through interaction with the surfactant, as evident by the low diffusion coefficients of D$_2$O in the AX-loaded medium compared to the unladed system. This means that astaxanthin has no direct interaction with the water, however, it affects the water mobility that is induced by the surfactant.

Other Lipophilic Agents

Astaxanthin was demonstrated above as a model lipophilic agent for extraction processes described herein. However, the process may be used to extract a variety of lipophilic agents from a variety from natural sources.

A number of plant sources containing active molecules were chosen to show the high effectiveness of the extraction medium for the extraction of various active molecules: piperine (extracted from black pepper corns), oleuropein (extracted from olive leaves), trimyristin (extracted from nutmeg), eugenol (extracted from allspice corns), curcumin (extracted from turmeric root), carotene (extracted from baby carrots), lycopene (extracted from dried tomatoes and

TABLE 5-1

Diffusion coefficients (m$^2$/sec), as measured by SD-NMR, unloaded extraction medium

| Water content (wt %) | Tween 80 | PG | R-(+)-limonene | EtOH | D$_2$O |
|---|---|---|---|---|---|
| 0 | 4.6 × 10$^{-12}$ | 4.53 × 10$^{-11}$ | 5.66 × 10$^{-11}$ | 4.58 × 10$^{-11}$ | — |
| 10 | 3.3 × 10$^{-12}$ | 4.74 × 10$^{-11}$ | 3.33 × 10$^{-11}$ | 4.85 × 10$^{-11}$ | 3.3 × 10$^{-11}$ |
| 20 | 1.5 × 10$^{-12}$ | 6.15 × 10$^{-11}$ | 1.36 × 10$^{-11}$ | 6.17 × 10$^{-11}$ | 1.35 × 10$^{-11}$ |
| 30 | 6 × 10$^{-13}$ | 8.55 × 10$^{-11}$ | 4.3 × 10$^{-12}$ | 8.67 × 10$^{-11}$ | 2.64 × 10$^{-10}$ |
| 40 | 5 × 10$^{-13}$ | 1.24 × 10$^{-10}$ | 1.5 × 10$^{-12}$ | 1.25 × 10$^{-10}$ | 3.88 × 10$^{-10}$ |
| 50 | 9 × 10$^{-13}$ | 1.68 × 10$^{-10}$ | 1.5 × 10$^{-12}$ | 1.65 × 10$^{-10}$ | 5.0 × 10$^{-10}$ |
| 60 | 2.2 × 10$^{-12}$ | 2.34 × 10$^{-10}$ | 3.3 × 10$^{-12}$ | 2.37 × 10$^{-10}$ | 6.34 × 10$^{-10}$ |
| 70 | 5.7 × 10$^{-12}$ | 3.19 × 10$^{-10}$ | 5.9 × 10$^{-12}$ | 3.3 × 10$^{-10}$ | 9.1 × 10$^{-10}$ |
| 80 | 1.09 × 10$^{-11}$ | 4.42 × 10$^{-10}$ | 1.15 × 10$^{-11}$ | 4.82 × 10$^{-10}$ | 1.13 × 10$^{-9}$ |
| 90 | 2.06 × 10$^{-11}$ | 6.03 × 10$^{-10}$ | 2.14 × 10$^{-11}$ | 5.82 × 10$^{-10}$ | 1.45 × 10$^{-09}$ |

TABLE 5-2

Diffusion coefficients (m$^2$/sec), as measured by SD-NMR, 0.5 wt % AX-loaded medium

| Water content (wt %) | Tween 80 | PG | R-(+)-limonene | EtOH | D$_2$O | AX |
|---|---|---|---|---|---|---|
| 0 | 4.5 × 10$^{-12}$ | 4.43 × 10$^{-11}$ | 5.46 × 10$^{-11}$ | 4.13 × 10$^{-11}$ | — | 4.7 × 10$^{-12}$ |
| 10 | 3.5 × 10$^{-12}$ | 4.78 × 10$^{-11}$ | 3.09 × 10$^{-11}$ | 4.66 × 10$^{-11}$ | 3.1 × 10$^{-11}$ | 3 × 10$^{-12}$ |
| 20 | 2.9 × 10$^{-12}$ | 4.86 × 10$^{-11}$ | 2.36 × 10$^{-11}$ | 4.78 × 10$^{-11}$ | 2.84 × 10$^{-11}$ | 1.4 × 10$^{-12}$ |
| 30 | 6 × 10$^{-13}$ | 8.69 × 10$^{-11}$ | 3.2 × 10$^{-12}$ | 8.67 × 10$^{-11}$ | 3.2 × 10$^{-12}$ | 3 × 10$^{-13}$ |
| 40 | 4 × 10$^{-13}$ | 1.23 × 10$^{-10}$ | 1.4 × 10$^{-12}$ | 1.2 × 10$^{-10}$ | 1.3 × 10$^{-12}$ | 3 × 10$^{-13}$ |
| 50 | 9 × 10$^{-13}$ | 1.75 × 10$^{-10}$ | 1.4 × 10$^{-12}$ | 1.7 × 10$^{-10}$ | 2.69 × 10$^{-11}$ | 7 × 10$^{-13}$ |
| 60 | 2.2 × 10$^{-12}$ | 2.41 × 10$^{-10}$ | 3.1 × 10$^{-12}$ | 2.33 × 10$^{-10}$ | 7.96 × 10$^{-10}$ | 1.4 × 10$^{-12}$ |
| 70 | 5.3 × 10$^{-12}$ | 3.35 × 10$^{-10}$ | 5.7 × 10$^{-12}$ | 3.32 × 10$^{-10}$ | 9.1 × 10$^{-10}$ | 4.8 × 10$^{-12}$ |
| 80 | 1.05 × 10$^{-11}$ | 4.67 × 10$^{-10}$ | 1.10 × 10$^{-11}$ | 4.67 × 10$^{-10}$ | 1.16 × 10$^{-9}$ | 1.12 × 10$^{-11}$ |
| 90 | 1.91 × 10$^{-11}$ | 6.03 × 10$^{-10}$ | 1.91 × 10$^{-11}$ | 5.89 × 10$^{-10}$ | 1.48 × 10$^{-09}$ | |

As can be seen from Tables 5-1 and 5-2, the diffusion coefficient of AX is similar to that of the surfactants (Tween 80 and R-(+)-limonene). These results indicate that the AX is located within the core and at the interface of the swollen micelle. As also evident from the results, AX solubilization causes the binding of water molecules through interaction with the surfactant. This suggests that all of the AX in the media is contained within the oil droplet, and it is likely that lycopene rich cherry tomatoes), lutein (extracted from marigold flowers), and betain and anthocyanins (extracted from beetroot).

According to the raw plant, pretreatment was optionally carried out. Olive leaves, nutmeg (grounded), and turmeric (grounded) were used as received. Black pepper and allspice were pounded with pestle and mortar and sieved. Beetroot, dried tomatoes and baby carrots were finely chopped and heated at vacuum oven for 1.5 hours at 60° C. Marigold flowers were washed and dried, and petals were separated and heated under vacuum for 1.5 hours at 60° C. Lycopene rich cherry tomatoes were mashed in a blender; half of the mashed tomatoes were centrifuged twice to remove most of the water. The other half was lyophilized for 20 hours.

Extraction was carried out as follow: plants samples were weighted, and then AX-1 extraction medium was weighted into the same flask. The ratios between the plant and the extraction medium were determined based on the plant and were within a range of 1:1 and 1:10. A Silverson homogenizer was used for homogenization for 30 min at room temperature (25-28° C.). At the end of the extraction, the slurry was centrifuged for 20 min for separating the loaded medium from the spent biomass. The loaded medium was filtered and kept in the fridge until been analyzed.

For the extraction of piperine and curcumin another series of 3 cycles of extractions was accomplished, using new plant source and loaded-ME at each cycle.

Droplet Size Measurements

The loaded-medium samples were diluted by 90 wt % water and droplet size was measured with DLS.

Figure 9A:
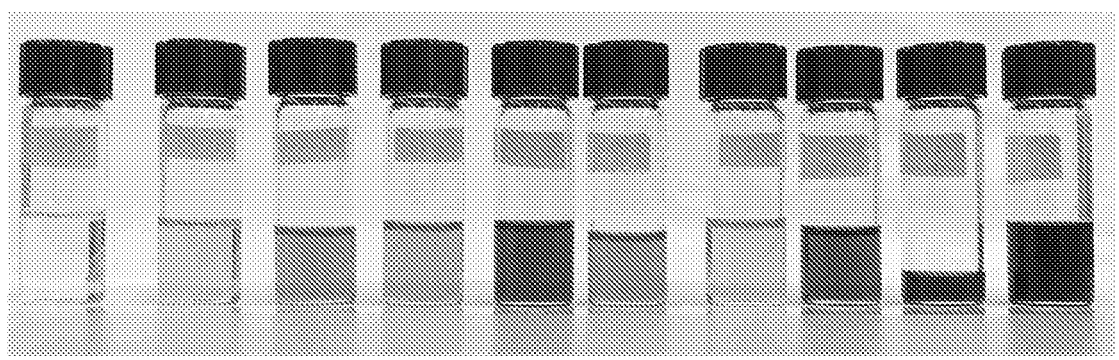
Figure 9B:

Table 6 presents the droplet size of the extracts from different plant sources as well as the polydispersity index. FIGS. 9A and 9B show the concentrates and diluted mediums, respectively.

TABLE 6

Droplet size and polydispersity index of agent-loaded mediums, 90 wt % water

| Plant source | Drop size [nm] | PDI |
| --- | --- | --- |
| Allspice | NA | NA |
| Black pepper | 12.05 ± 0.45 | 0.15 ± 0.01 |
| Nutmeg | 14.92 ± 0.32 | 0.27 ± 0.32 |
| Olive leaves | NA | NA |
| Turmeric | 11.84 ± 0.19 | 0.21 ± 0.01 |
| Tomatoes | 12.03 ± 0.26 | 0.14 ± 0.03 |
| Carrots | 11.55 ± 0.21 | 0.18 ± 0.02 |
| Marigold flower | 11.57 ± 0.01 | 0.17 ± 0.01 |
| Beetroot | 18.33 ± 0.37 | 0.36 ± 0.01 |
| Empty system | 11.24 ± 0.26 | 0.115 ± 0.024 |

Concentration of Active Molecules in the Medium and Yield of the Extraction

One Step Extraction

Extraction products from black pepper, turmeric, tomato paste, and lyophilized tomato were diluted with distilled water or organic solvents (ethanol or acetone) at $10^2$-$10^3$ order of magnitude. UV-visible spectrum of the dilutions were recorded against suitable blank and absorption at the chosen wavelength was taken for the determination of the component in the extract. A spectrum of standards was recorded for each agent, from which the wavelength at the maximum was chosen as the wavelength at which calibration curve was constructed based on Beer-Lambert law. Further calculation based on reported data about plant capacity of each nutraceutical were carried out to determine the yield of the extraction. Table 7 details the concentration of the active molecules in the agent-loaded mediums and the yield of the extraction.

TABLE 7

The concentration of the active molecules and yield of the extraction after one cycle

| Active molecule | Source | λmax [nm] | Concentration in plant source | Concentration in medium [mg/g] | Yield of extraction [%] |
| --- | --- | --- | --- | --- | --- |
| Piperine | Black pepper (grounded) | 310 | 5-9% [2] | 12.48 | 69.3-89.2 |
| Curcumin | Turmeric (grounded) | 424 | 0.58-3.14% [3] | 2.02 | 32.2-50.5 |
| Lycopene | Tomato paste | 480 | 340 ppm [4] | 0.04 | 57.9 |
|  | Lyophilized tomatoes | 480 | 900-1200 ppm [5] | 0.05 | 40.6-58.1 |

Yield determined according to range of concentrations of component in the plant

Multi-Step Extraction

Figure 10A:
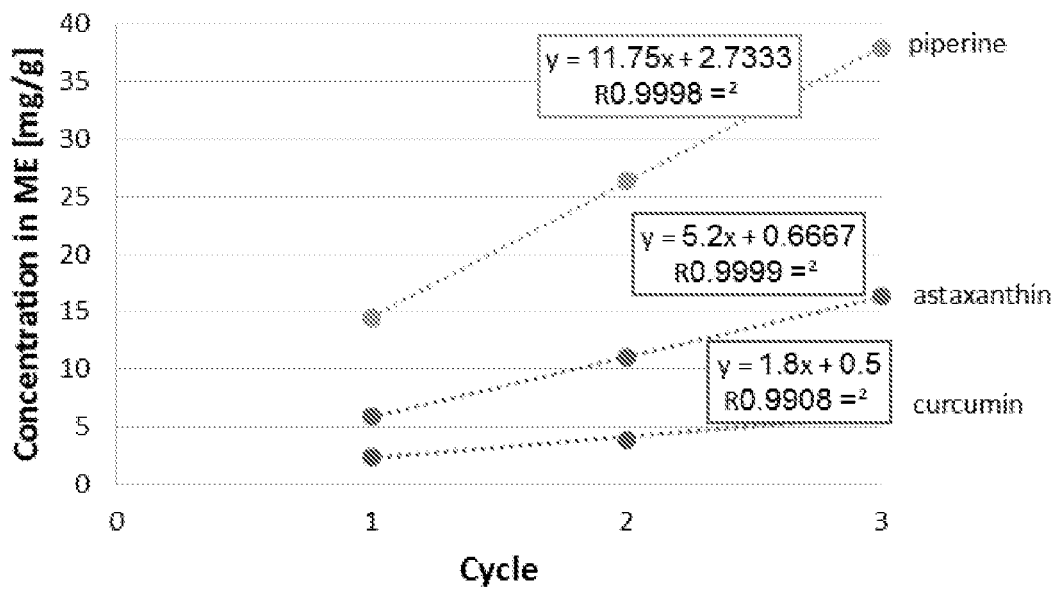
Figure 10B:
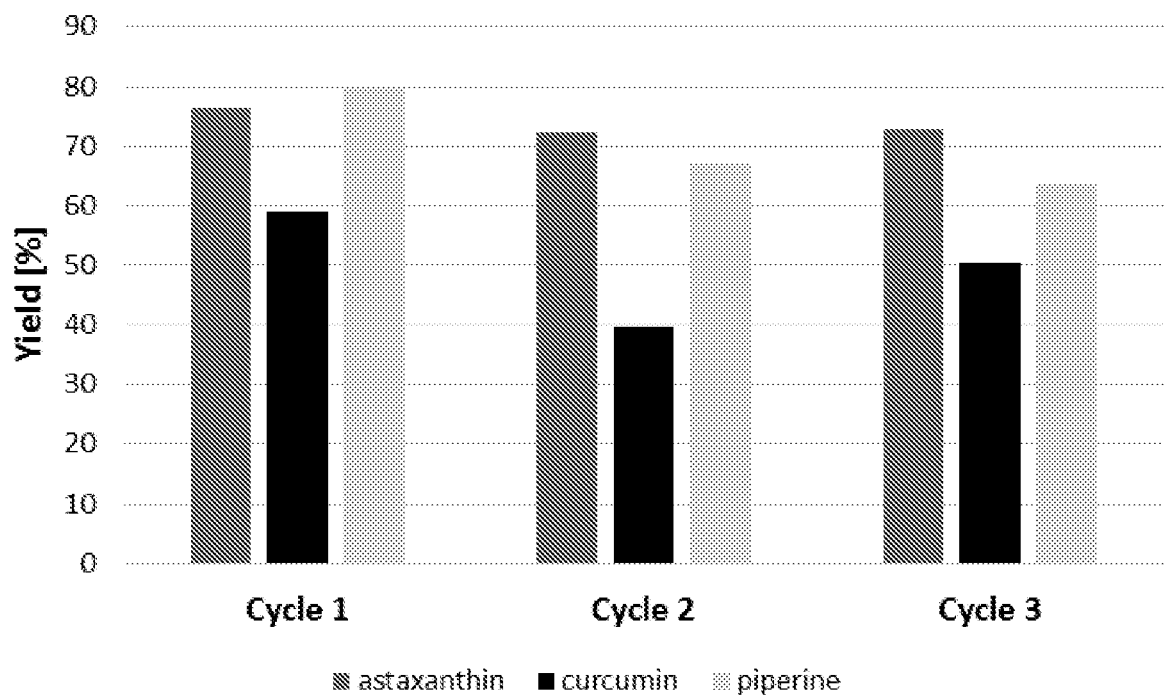

Extraction products from black pepper and turmeric were diluted with ethanol or acetone at $10^3$-$10^4$ order of magnitude. Analysis was the same as in case of one step extraction. FIG. 10A shows the concentrations of curcumin and piperine, as compared to astaxanthin, in the medium after one, two and three cycles. Linear fit was plotted for each component. FIG. 10B shows the yield of the extraction at each of the three cycles for astaxanthin, curcumin and piperine.

As clearly evident, the extraction mediums and process described herein demonstrate the ability to extract various molecules from their natural source, which appears in a variety of forms. As also evident, for the same extraction medium formulation, different concentrations and yields were achieved for each extracted molecule, suggesting that selectivity of extraction may be controlled by tailoring the composition of the microemulsion to the desired molecule to be extracted.

Further exemplary target molecules which were extracted by AX-1 extraction medium formulation were rosmanol acid (extracted from rosemary leaves), cinnamaldehyde (extracted from cinnamon bark), chlorogenic acid (extracted from green coffee beans), and omega 3 fatty acid (extracted from chia seeds).

Cinnamon and chia seeds were used as received. Green coffee beans were ground and pounded by pestle and mortar. Rosemary was either chopped or heated for 13 min before the extraction.

Extraction was carried out as detailed above. Initial characterization results are provided in Table 8.

TABLE 8

Characterization of mediums loaded with the active molecules

| Active molecule | Drop size [nm] | Viscosity of concentrate [µS/cm] |
| --- | --- | --- |
| Rosmarinic acid | 21.41 (±0.36) | 0.129 (±0.013) |
| Cinamaldehyde | 17.87 (±0.97) | 0.141 (±0.002) |
| Chlorogenic acid | 11.45 (±0.77) | 0.093 (±0.009) |
| Linolenic acid | 26.05 (±0.97) | NA |

The invention claimed is:

1. A process for extraction of a lipophilic agent from a plant source, the process comprising:
   (a) mixing a first quantity of a plant source, the plant source containing the lipophilic agent and a first quantity of an extraction medium to obtain a first mixture, the extraction medium being in the form of a microemulsion and comprising at least one oil, at least one hydrophilic surfactant, at least one co-surfactant and optionally at least one co-solvent;
   (b) homogenizing the first mixture under conditions maintaining the microemulsion structure; and
   (c) separating the homogenized mixture into a biomass slurry and an agent-loaded medium to obtain the agent-loaded medium in a microemulsion form.

2. The process of claim 1, wherein the agent-loaded medium comprises between about 0.02 and 20 wt % of the lipophilic agent.

3. The process of claim 1, wherein the homogenization of step (b) is carried out in at least one condition selected from (i) a period of time of between about 1 minute and about 120 minutes, (ii) at a pressure of between about 500 and 6,000 psi, and (iii) at a temperature of between about 5 and about 70° C.

4. The process of claim 1, wherein the weight ratio (wt/wt) of the first quantity of plant source to the first quantity of extraction medium is between 1:5 and 1:80.

5. The process of claim 1, further comprising:
   (d) mixing the biomass slurry with a second quantity of the extraction medium being in the form of a microemulsion to obtain a second mixture;
   (e) homogenizing the second mixture; and
   (f) separating the second mixture into biomass slurry and agent-loaded medium to obtain the agent-loaded medium in a microemulsion form.

6. The process of claim 1, further comprising:
   (d') mixing the agent-loaded medium in a microemulsion form with a second quantity of the plant source to obtain a second mixture;
   (e') homogenizing the second mixture; and
   (f') separating the second mixture into biomass slurry and highly agent-loaded medium in a microemulsion form.

7. The process of claim 1, wherein said at least one oil is selected from the group consisting of essential oils, D-limonene, mineral oil, paraffinic oils, phospholipids, polar lipids, squalenes, sphingomyelins, waxes, vegetable oils, glycerides, triglycerides, fatty acids and esters of fatty acids, and liquid hydrocarbons, wherein said at least one oil being present in the extraction medium at an amount of between about 0.5 and 20 wt %.

8. The process of claim 1, wherein said at least one hydrophilic surfactant is selected from the group consisting of polyethylene glycol (15)-hydroxystearate (Solutol HS15), polyoxyethylene sorbitan monolaurate, polyoxyethylene sorbitan monopalmitate, polyoxyethylene sorbitan monooleate, and polyoxyethylene esters of saturated and unsaturated castor oil, ethoxylated monoglycerol esters, ethoxylated fatty acids, ethoxylated fatty acids of short, medium and long chain fatty acids, wherein said at least one hydrophilic surfactant being present in the extraction medium at an amount of between about 30 and 85 wt %.

9. The process of claim 1, wherein said at least one co-surfactant is selected from the group consisting of polypropylene glycol, polyethylene glycol, sorbitol, xylitol, PEG 200, PEG 400 and PEG 600, wherein said at least one co-surfactant being present in the extraction medium at an amount of between about 1 and 50 wt %.

10. The process of claim 1, wherein the extraction medium further comprises at least one phospholipid, in an amount of between about 1 and 10 wt % of phospholipids; and/or at least one solvent, wherein the extraction medium comprises between about 0.1 and 25 wt % of said solvent.

11. The process of claim 1, wherein the extraction medium is essentially free of water.

12. The process of claim 1, wherein the lipophilic agent to be extracted is selected from the group consisting of astaxanthin, lycopene, beta-carotene, lutein, eugenol, piperine, anthocyanins, betain, oleuropein, trimyristin, curcumin, capsaicin, gossipol, rosmanol, chlorogenic acid, cynamaldehyde, flavones, caffeine, isoflavone, tocopherol, omega fatty acids (including DHA and EPA), caffeic acid, niacin, nicotinamide, flavonoids, cineole, borneol, thujone, carnosol, carnosic acid, fumaric acid, behenic acid; and any triglycerides, or esters of long chain fatty acids of the lipophilic agent.

13. The process of claim 1, wherein the plant source is an algae or a microalgae.

14. The process of claim 13, wherein the microalgae is *Haematococcus pluvialis* and the lipophilic agent is astaxanthin.

* * * * *